United States Patent
Al Jasim et al.

(10) Patent No.: US 11,260,097 B2
(45) Date of Patent: Mar. 1, 2022

(54) IMMUNOMODULATORY COMPOSITION TO TREAT AND/OR PREVENT COVID-19 ILLNESS

(71) Applicant: COVImmune Pharma LLC, Lynnwood, WA (US)

(72) Inventors: Nedaa Abdul-Ghani Nasif Al Jasim, Lynnwood, WA (US); Noor Z. Ahmed, Lynnwood, WA (US)

(73) Assignee: COVImmune Pharma LLC, Lynnwood, WA (US)

( * ) Notice: Subject to any disclaimer, the term of this patent is extended or adjusted under 35 U.S.C. 154(b) by 0 days.

(21) Appl. No.: 16/920,961

(22) Filed: Jul. 6, 2020

(65) Prior Publication Data

US 2022/0000958 A1    Jan. 6, 2022

(51) Int. Cl.
*A61K 36/71*    (2006.01)
*A61P 31/14*    (2006.01)

(52) U.S. Cl.
CPC .............. *A61K 36/71* (2013.01); *A61P 31/14* (2018.01); *A61K 2236/333* (2013.01)

(58) Field of Classification Search
CPC .... A61K 36/71; A61K 2236/333; A61P 31/14
See application file for complete search history.

(56) References Cited

U.S. PATENT DOCUMENTS

| | | |
|---|---|---|
| 5,482,711 A | 1/1996 | Medenica |
| 7,592,327 B2 | 9/2009 | Nassief |
| 10,588,930 B2 | 3/2020 | Al Asoom |
| 10,729,735 B1 | 8/2020 | Newman et al. |
| 2020/0054704 A1 | 2/2020 | Madhavamenon et al. |

FOREIGN PATENT DOCUMENTS

| | | |
|---|---|---|
| FR | 2925898 A1 | 7/2009 |
| WO | 2016159582 A2 | 10/2016 |

OTHER PUBLICATIONS

Koshak et al, "Nigella sativa L as a potential phytotherapy for coronavirus disease 2019: A mini review of in silico studies" Jul. 2020 Curr. Then Res, 93, 2020, 100670, 3 pages. (Year: 2020).*

Guo et al "Effect of Thymoquinone on Acute Kidney Injury Induced by Sepsis in BALB/c Mice" BioMed Research International, Jun. 16, 2020, vol. 2020, Article ID 1594726, 7 pages; doi:/10.1155/2020/1594726. (Year: 2020).*

Palmer, Doug "Biden team says it supports waiving patent protections on Covid-19 vaccines" Politico LLC, May 5, 2021, <URL: politico.com/news/2021/05/05/biden-covid-vaccine-patent-protections-485458>, 5 pages. (Year: 2021).*

Nde, D et al. "Optimization methods for the extraction of vegetable oils: A review." Processes 8, No. 2 (2020): 209.

Zhang, QW et al. "Techniques for extraction and isolation of natural products: a comprehensive review." Chinese medicine 13, No. 1 (2018): 20.

* cited by examiner

*Primary Examiner* — Aaron J Kosar
(74) *Attorney, Agent, or Firm* — Michael G. Monyok

(57) ABSTRACT

A novel process for extraction of the bioactive phytochemicals from herbs to provide a composition that boost antiviral innate immune response and induce interferon secretion in a host affected by COVID-19 illness and in need for such immunomodulatory treatment.

12 Claims, 11 Drawing Sheets

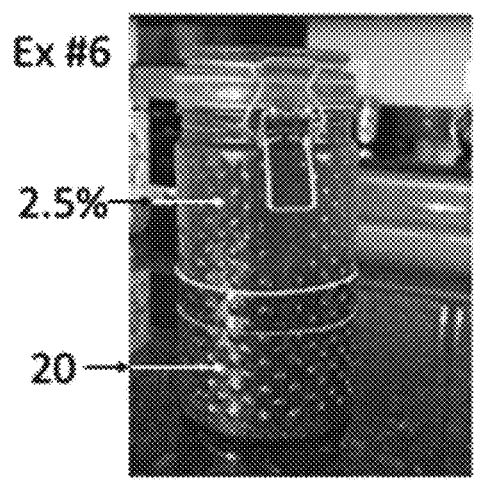
Figure 13
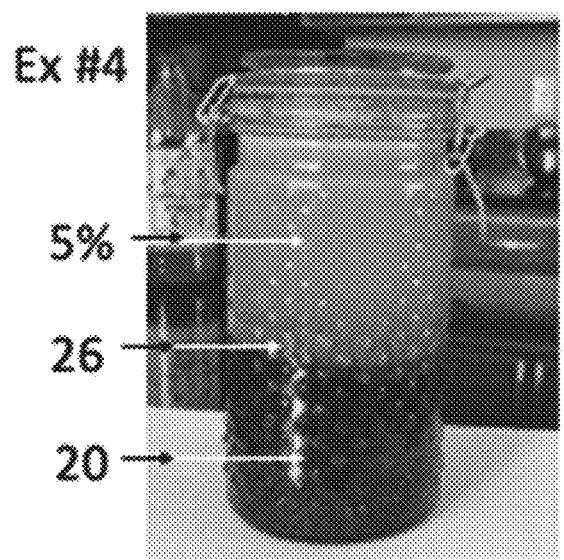 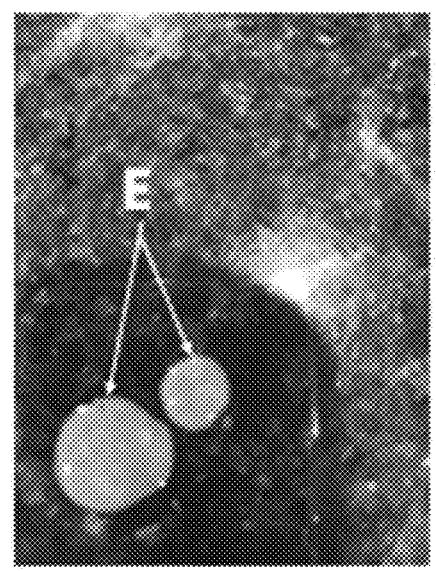
Figure 14A  Figure 14B

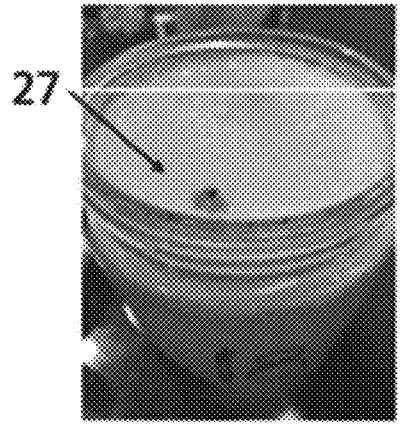 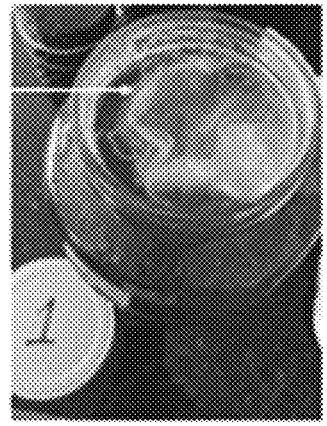
Figure 18A  Figure 18B
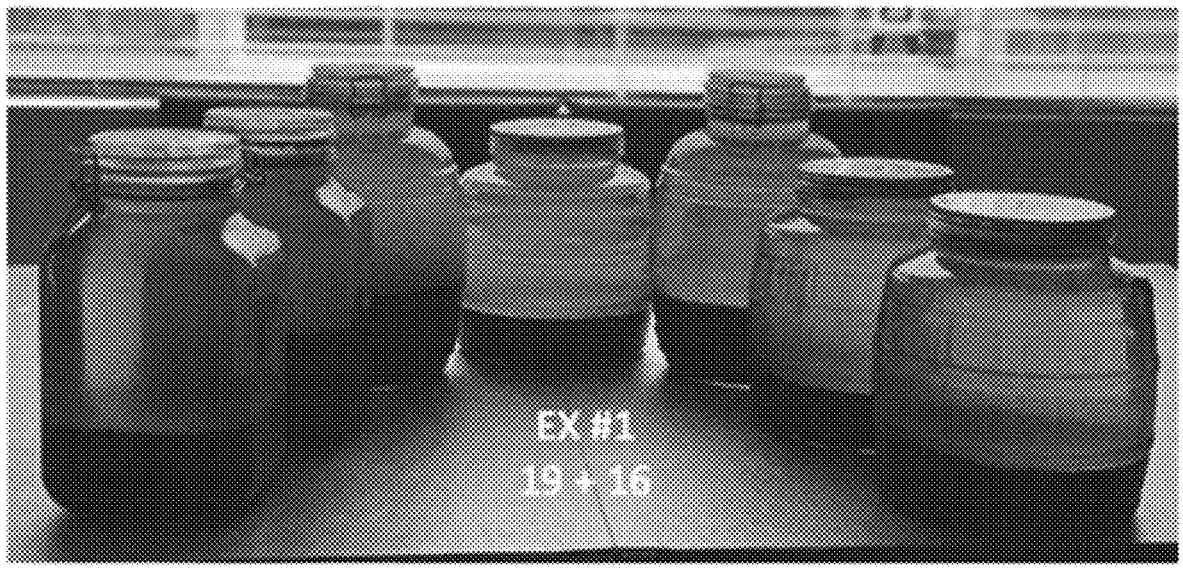
Figure 19

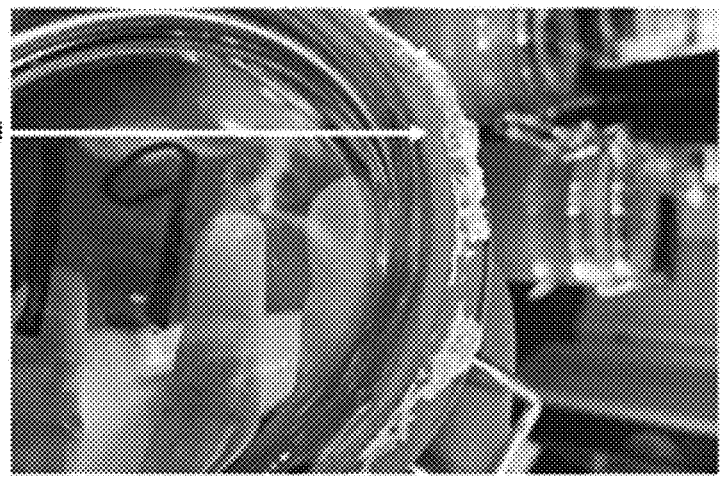
Figure 22
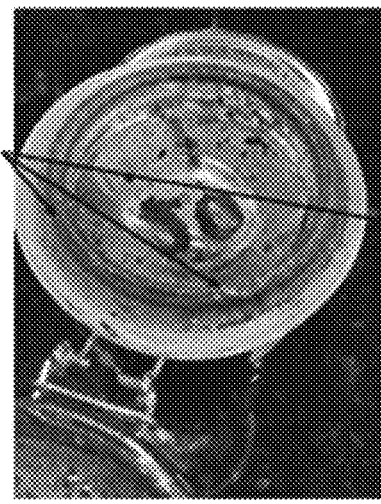 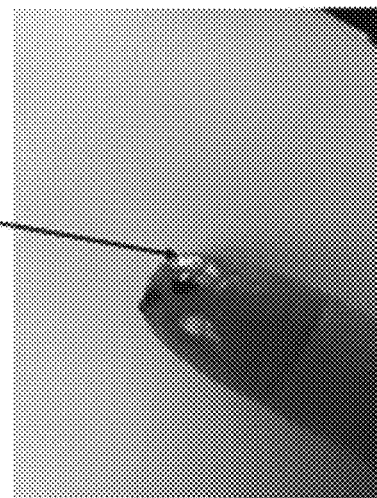
Figure 23A  Figure 23B

IMMUNOMODULATORY COMPOSITION TO TREAT AND/OR PREVENT COVID-19 ILLNESS

CROSS-REFERENCE TO RELATED APPLICATIONS

Not applicable.

STATEMENT REGARDING FEDERALLY SPONSORED RESEARCH

Not applicable.

BACKGROUND OF THE INVENTION

The present invention relates to the field of health protective complimentary medicine, pharmaceutical preparation and nutritional supplement, more particularly to a process of acid extraction bio-fermentation and incubation of *Nigella sativa* seeds for preparing a composition having the immunomodulatory/antiviral bioactive phytochemicals of the seeds of *Nigella sativa* to treat and/or prevent COVID-19 illness.

The COVID-19 pandemic is an ongoing global pandemic of coronavirus disease 2019, caused by coronavirus 2 (SARS-CoV-2). The COVID-19 outbreak was first identified in December 2019. There is no drug presently approved by the FDA to prevent and treat COVID-19, antiviral medications are under investigation and none has yet been shown to be clearly effective in clinical trials.

Researchers are investigating whether existing medications can be used effectively against COVID-19 or the immune reaction to the virus. chloroquine and hydroxychloroquine, the antimalarial drugs, have been in the headlines as potential treatment for COVID-19. The molecular mechanism of both drugs is related to their immunomodulating action.

Chloroquine is an alkaloid of plant origin discovered from the bark of cinchona tree, and hydroxychloroquine is the synthetic analogue that expand the horizon for clinical application of chloroquine (Shukla and Shukla, 2020).

Related to this invention, immunomodulating alkaloids nigellidine, nigellimine and nigellicine are found in the folklore medicinal plant *Nigella sativa* Linn of Ranunculaceae family.

Why *Nigella sativa* is selected to treat COVID-19 illness?

In this invention, a novel process of extracting the bioactive phytochemicals of *Nigella sativa* seeds of acid extraction/bio-fermentation of *Nigella sativa* seeds using aqueous ethanoic acid solution under cold temperature.

The composition obtained is claimed to treat COVID-19 illness based on the following overwhelming scientific evidence:

1—The fact that many people infected with SARS-CoV-2 will clear the virus, with only mild symptoms, suggests that the innate immune system, namely interferon secreted from within, may hold the key to defeat this virus. Harnessing innate immunity could act as a trojan horse "danger" signal which favorably tricks the host into thinking that immune responses are required (Golonka et al., 2020).

2—*Nigella sativa* is a well-known for its effect as an immunomodulating herb that boost the 3 components of the innate immune system: interferon (INF), natural killer lymphocytes (NK) and dendritic cells (DCs) (Maurya et al., 2020; Islam et al., 2020; Singh et al, 2018; Ikhsan et al., 2018; Shabsoug et al., 2008; Salem, 2005; Majdalawieh and Fayyad, 2016; Islam et al., 2017; Xuan et al., 2010; Khan et al., 2011).

3—*Nigella sativa* have demonstrated anti-viral properties, decreasing viral loads and achieving sero-negative conversion in 51 patients with human immunodeficiency syndrome (HIV) (Onifadee et al., 2011; Ma et al., 1994; Aljabre et al. 2015) and hepatitis C (Barakat et al. 2013; Yimer et al., 2019; Oyero et al., 2016).

4—The good news is that, Bouchentouf and Noureddine (2020) have identified new probable inhibitors of COVID-19 by molecules from NS, by acting on the main protease ($M^{pro}$). Results by molecular docking showed that Nigellidine and alpha-heridin are main compounds from NS which inhibit COVID-19, giving the same or better energy score compared to drugs under clinical tests including chloroquine, hydroxychloroquine.

5—*Nigella sativa* have a BCG-like activity: In 1999, the current inventor conducted a research to find a causal-relationship between virus respiratory infection and asthma exacerbation. Extracts of *Nigella sativa* were tested using H3 thymidine incorporation compared to BCG [purified protein derivative of *Bacillus* Calmette Guerin (PPD)]. *Nigella sativa* extracts were found to be identical to BCG (UK patent publication #GB2348139, granted in 2004, PCT, and U.S. Pat. No. 7,592,327, B2). Currently, multiple clinical trials are being conducted to evaluate the therapeutic/preventive benefits of vaccinating health workers with BCG vaccine.

6—*Nigella sativa* seed extract stimulate the expression of virus recognition TLR-4 in rat macrophages; increased phagocytic activity and increased TLR-4 receptors expression using ELISA test (Akrom and Mustofa, 2017).

Ongoing Clinical Trials Using Immunomodulators and Cell Therapeutics for COVID-19:

In the race to find a COVID-19 treatment, and based on the science of the innate immune responses, multiple clinical trials are being conducted:

1—*Nigella sativa* and honey trial NCT04347382.
2—Chloroquine clinical trial NCT04333732.
3—Recombinant IFN-I/III administration NCT04343976, NCT04331899. Previous study of the role of IFNs in other betacoronaviruses infection report that exogenous type I IFN does not improve outcomes suggesting that the role of IFN option may be species specific (Vabret et al., 2020). Researchers at Stanford Medicine are leading a clinical trial of interferon-lambda for COVID-19.
4—Repurposed NK cells: Green Cross LabCell, Celularity Cell Therapy, NCT04280224.
5—Repurposed DCs: Lineage Cell Therapeutics.
6—BCG vaccination NCT04379336.
7—Chinese herbal medicines: Chinese red sage, honeysuckle oral liquid for boosting immunity and treat coronavirus pneumonia, and others (Vabret et al., 2020).

The problem with the above-identified therapies, that the innate immune system is an integrated web; therapeutic approaches that focus on individual component within this complex biologic system are inherently limited in both scope and potential (Menachery and Baric 2013; Lee and Ashkar, 2015).

The problem with *Nigella sativa* is that it has no patent protection.

To overcome the above problems, we are proposing a novel process of extracting an immunomodulating composition from the seeds of *Nigella sativa* seeds that is effective to "harness" endogenous interferon together with NK and DCs, 3-in-one therapeutic approach.

FIG. 1 demonstrate molecular mechanisms of body response to COVID-19 virus (V) infection of the respiratory epithelial cell (1) and airway resident NK cell (2), DCs (3) and T-helper cell (T1). The virion is attached to pathogen-recognition receptor, including Toll-like receptors (TLR) (4); communicate viral threat between infected and non-infected cells inducing antiviral state (Miura T, 2019). An initial wave of interferon is produced at 12 hours dependent on IRF (5) phosphorylation; signaling through IFN receptor (6); expression of IFN-stimulated gene (7); a second wave of interferon is produced at 48 hours post-infection; IFN (8) is secreted to protect neighboring cells and kick start systemic antiviral response to clear the infection (9) and generate a "trained" innate immune responses with activated natural killer cells receptor (NCR) and mature dendritic cell to engulf phagocytose virus-infected cells (PH).

FIG. 2 demonstrate the proposed immunomodulatory mechanisms of *Nigella sativa* composition (ImMod) as a treatment for COVID-19 by acting of the innate immune cells of the gut-associated lymphoid tissue activating gut-resident NK cells (G2) and maturating gut-resident DCs (G3); inducing INF secretion.

FIG. 3 demonstrate the BCG like activity of *Nigella Sativa* extracts (11, 12 and 13) vs. BCG (14) and phytohaemagglutinin (15).

Current Methods of Extraction of *Nigella Sativa:*

Methods of extraction of *Nigella sativa* are disclosed in U.S. patent Ser. No. 16/663,714, inventors Madhavamenon et al.; U.S. patent Ser. No. 15/710,212, inventor Al Asoom, 2019; U.S. Pat. No. 5,482,711, inventor Medenica, 1996.

Methods of extraction of *Nigella sativa* extracts are numerous. Selection of the method of extraction depends on the intended use of the extract that can be classified into:

A. Extracts for laboratory testing and experimentation, i.e., extraction of NS seeds using chloroform as a solvent for the experiment of H3 thymidine incorporation test in FIG. 3. This extract is not suitable for human use B. Extract for use in a human subject with an intention-to-treat.

According to the EU Directive 2009/32/EC on extraction solvents used in the production of foodstuffs and food ingredients, "extraction solvent" means a solvent which is used in an extraction procedure during the processing of raw material, of food stuff, or of components or ingredients of these products and which is removed but which may result in the unintentional, but technically unavoidable, presence of residues or derivatives in the foodstuff or food ingredient.

Solvents can leave undesirable taste or smell in the extract, and might be unsafe for human use.

The *Nigella sativa* products that are commercially available for human consumption is the cold press oil in containers under different trade names. In addition, NS oil capsules are available as soft gel capsules from multiple manufacturers online and in local shops.

Volatile oils from NS seeds are extracted by water distillation and soxhalation and supercritical liquid extract.

Ma et al., 2019 studied the optimum extraction technology for the seed oil of *Nigella sativa* L. in relation to different parameters including grinding degree, extraction temperature, liquid-seed ratio, and extraction time.

The methods of extraction of vegetable oils from oilseeds have been recently reviewed by Nde and Foncha, 2020. It includes an exhaustive list of methods currently used. The list of methods described are similar to methods used to extract NS oil.

NS preparations were obtained either by physical, chemical, enzyme-assisted or supercritical fluid extraction methods or a combination thereof (Mohammed et al., 2016):

A. Physical Extraction Methods:
   a. Cold press oil technique is the most common method used to extract NS oil present in the market. The procedure was described by Bordoni et al. (2019) as cold pressing NS seeds using a squeezing machine, the squeezed oil is filtered after 10 days to remove solid material.
   b. Bourgou et al., 2010 studied the bioactivities of black cumin essential oil and its main terpenes. The essential oil was obtained from seeds (100 g) by hydrodistillation for 90 min in a Clevenger type apparatus. The oil was then dried with anhydrous sodium sulphate and stored at −20° C. in darkness until used.

B. Chemical Extraction Methods: NS seed extraction with a spectrum of solvent ranging from hydrophilic, lipophilic or commercial products of NS oil (Koshak et al., 2018).
   a. Hydrophilic solvents are the aqueous water extracts prepared and used in different experimental settings.
   b. Lipophilic solvents used in experimental designs include 1-Methanol, 2-Ethanol, 3-Butanol, 4-Diethyl ether, 5-n-Hexane and 6-Acetone (Ishtiaq, 2013), 7-Petroleum Ether and 8-Chloroform (Khoddami et al., 2011). Liquified dimethyl ether is used for efficient extraction of thymol (Subratti et al., 2019).
   c. Solvents-assisted extraction of thymoquinone is performed using Soxhlet apparatus (designed in 1800s) using methanol and n-hexane combined in different proportion in a lengthy multistep process (Butt et al., 2019)

C. Enzymatic-Assisted Extraction: NS Oil is expressed from their seeds with different types of enzymes including Hemicellulase, Pectinase, Acid Protease, Protease and Cellulase. Enzymes are useful for extraction give better yield and catalyzed the reaction by minimizing residence time (Gawankar et al., 2016). Enzyme-assisted supercritical extraction of *Nigella sativa* seed (Madhavamenon et al., U.S. patent application Ser. No. 16/663,714, published on Feb. 20, 2020)

D. Supercritical fluid extraction (SFE) is currently a technique among others used to extract plant oils and offers some favorable features over the traditional techniques that have been used in the oil industry. In general, SFE has been the recommended method used to extract antioxidant compounds from NS oil and exhibits a higher concentration of thymoquinone (Mohammed et al., 2016; Venkatachallam et al., 2010).

E. Microwave-Assisted Extraction, Xue et al. 2014 refers to patent #CN104672075A (China) a microwave-assisted solvent extraction process to separate thymoquinone in *Nigella* plant seeds by virtue of silica gel column chromatography.

F. Ultrasound-assisted extraction technique (Kausar et al., 2017).

G. Recently, the alkaloids and thymoquinones present in NS could now be obtained by total synthesis and the study of their pharmacological properties should make very interesting research studies for the future (Khan and Afzel, 2016). The synthetic NS compounds are claimed for use to treat COVID-19 as part of Innate Immunity Inducers.

Babar et al., 2018, proposed a simple method for extracting both active oily and water-soluble extract from *Nigella sativa* seeds using a single solvent system. This study provides a way of extraction for both active NSO and WSE from *Nigella sativa* seeds using 98% methanol. About 1 kg of ground seeds was macerated by 1:2.5 w/v (g/mL) for 72 hours. After rotary evaporation and 7 days of continuous drying and chilling at 50 and 4° C., NSO and WSE were obtained at the same instant.

Thilakarathna et al., 2018, proposed the decortication of *N. sativa* seed by removing the outer black coat before oil extraction. The technical goal is to remove the black pigment which is coming into the oil giving the product an undesirable color. As the seed length is 2-3 millimeters a prototype decorticator was designed and fabricated. Further, the author observed the effect of decortication under a Scanning Electron microscope. Decorticated seed will provide a new business venture as the product is more attractive.

Rao (1955) have described some criteria for the "ideal" solvent for vegetable oils extraction as: 1—It should be selective for the oil, and should not extract the pigment with the oil, 2—It should easily wet and penetrate the flakes of the oilseed, 3—Should be easily removable from the oil, 4—the solvent vapor is not toxic, 5—not inflammable at higher temperatures.

It is clear that, there is no single solvent known in the prior art that will satisfy these criteria.

In this invention we are proposing a process of extracting bioactive phytochemicals of *Nigella sativa* advantageously avoiding the use of hazardous solvent use the are environment friendly and safer for human consumption and healthy life style.

In this invention we are proposing a process of extracting bioactive phytochemicals of *Nigella sativa* advantageously avoiding the use of excessive heating (cold extraction) and therefore commercially feasible, environment friendly and safer for human consumption and healthy life style.

SUMMARY OF THE INVENTION

The current invention discloses a process of extraction of *Nigella* plant parts which comprises the use of carboxylic acid as the extraction solvent; its' mother of vinegar as the bio-fermentation microorganism; and further incubating the extract for a period of 1 to 40-days and beyond at cold temperature.

A preferred embodiment of the current invention is to use ethanoic acid in aqueous solution as the extraction solvent for *Nigella sativa* (NS) seeds in a concentration between 0.1-20% acidity in water.

One embodiment is that the ethanoic acid is either unpasteurized and unfiltered that contains the living active mother of vinegar or pasteurized and filtered with no mother.

One embodiment of the current invention is to use whole, either coarse or fine grinded, flaked, or powdered *Nigella sativa* as the substrate for extraction.

A preferred embodiment of the current invention is to soak grinded NS seeds using ethanoic acid 5% acidity to fill part of ¼-½ of the jar for a period between 1 to 8-hours.

One embodiment of the current invention is to fill-up the jar either with water or the extraction solution so that the final acidity of the solvent is between 1.25-5% acidity.

One embodiment of the current invention is to incubate the composition of acid extraction/bio-fermentation of NS seeds under either anaerobic condition by closing the filled-up jar with air-tight cover or under aerobic condition by closing the jar with a loose cover or by filling the jar partially.

One embodiment is to incubate the acid extracted composition for a duration of 1 to 40 days and even for a longer period to allow for the mother of vinegar to act on any components in the composition and the black pulp of the NS seed that can be fermented.

In a preferred embodiment a coarsely grinded NS seeds is extracted using ethanoic acid aqueous solution 1.25% acidity, under anaerobic conditions to provide a clear honey-colored composition.

In another preferred embodiment a coarsely grinded NS seeds is extracted using ethanoic acid aqueous solution 5% acidity under anaerobic conditions to provide an emulsion product.

In a preferred embodiment the composition is incubated at room temperate for 1-40 days to provide novel extracted components including pure white precipitate or crystal-like oil droplet or mother of *Nigella sativa*.

According to an embodiment of the present invention the NS composition comprises ALL the bioactive phytochemicals described for NS seeds in the prior art, in particular immunomodulating and antiviral therapeutic effect.

The process of aqueous acid extraction/bio-fermentation and incubation of the present invention provides a composition that contains the active pharmaceutical ingredient (API) for the manufacturing of a pharmaceutical drug or the bioactive phytochemicals of NS for use by itself as a complimentary immune boosting medicine or as a food supplement.

In a preferred embodiment the current invention provides a composition that potentially train, educate and induce interferon; natural killer; dendritic; and T cells of innate immune system named as "innate immune triad" that have a beneficial effect to treat and prevent COVID-19 illness.

This assumption is based on the cellular and molecular mechanism of action of the selected active composition in the elimination of viruses in a host in need for such treatment and prevention. Herein, this therapy is referred to as the "Innate Immune System Stimulating drugs" (InStim).

In an additional embodiment the current invention provides a composition that potentially possess antiviral property in human subjects and in animal models or vitro experiments that have a beneficial effect to treat and prevent COVID-19 illness.

In a preferred embodiment the current invention provides a composition that potentially possess antibacterial, anti-inflammatory, antioxidant beneficial effects that will add to the immunomodulatory mechanisms of molecular action that is incorporated herein because it is relevant to the outcomes of treatment or prevention of COVID-19 illness in additive manner. More detailed discussion will follow below.

BRIEF DESCRIPTION OF THE DRAWINGS

FIG. 13 demonstrate example #4, that depicts a jar that contains a composition of finely grinded NS seed in 2.5% ethanoic acid with mother of vinegar, under anaerobic condition.

FIG. 14A demonstrate example #5, that depicts a jar that contains a composition of finely grinded NS seed in 5% ethanoic acid with mother of vinegar, under anaerobic condition.

FIG. 14B demonstrate the appearance of a drop of the emulsion of example #4 on a table top.

FIG. 18A depicts thick new mother of NS at the mouth of the container in anaerobic container. FIG. 18B depicts thin new mother of NS at the mouth of the container in anaerobic container.

FIG. 19 depicts reproducibility of the type of the composition of coarsely-grinded NS in 1.25% ethanoic acid of Exp. #1.

FIG. 22 depicts NOVEL white solid precipitate emerged from saturated liquid composition.

FIG. 23A, FIG. 23B, FIG. 23C and FIG. 23D depicts NOVEL water-miscible oil as seen, felt, concentrated after evaporation and seen as dispersed droplets on a glass surface.

DETAILED DESCRIPTION OF THE INVENTION

Figure 1:
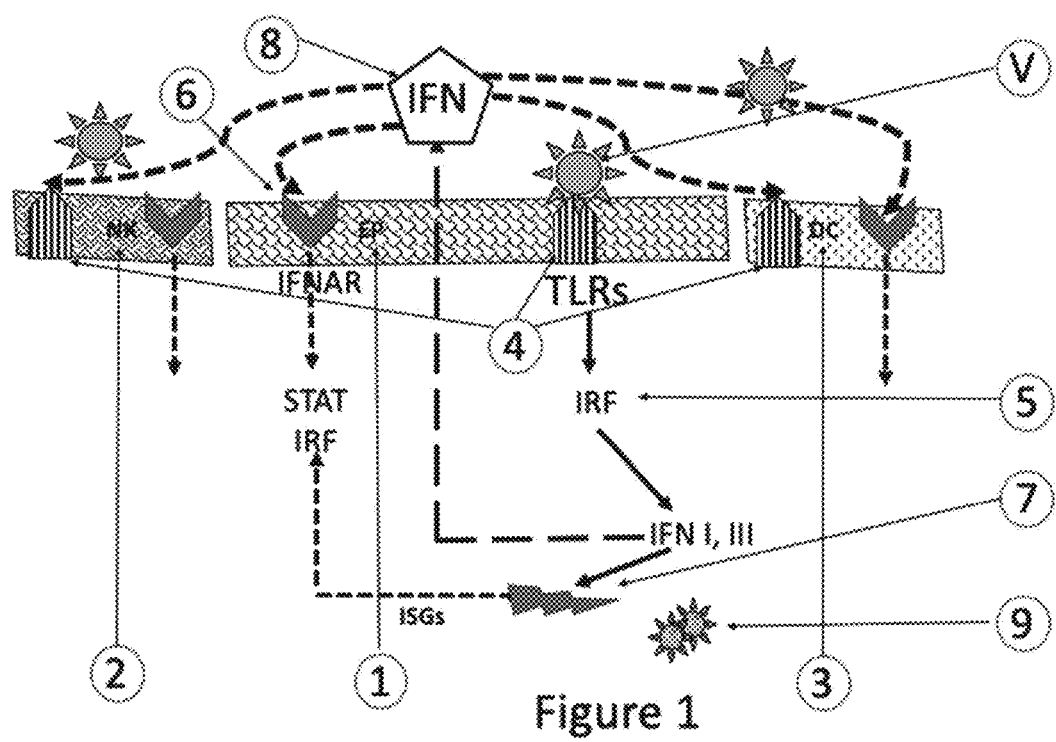
FIG. 1 demonstrate the molecular mechanisms of body response to COVID-19 virus.
Figure 2:
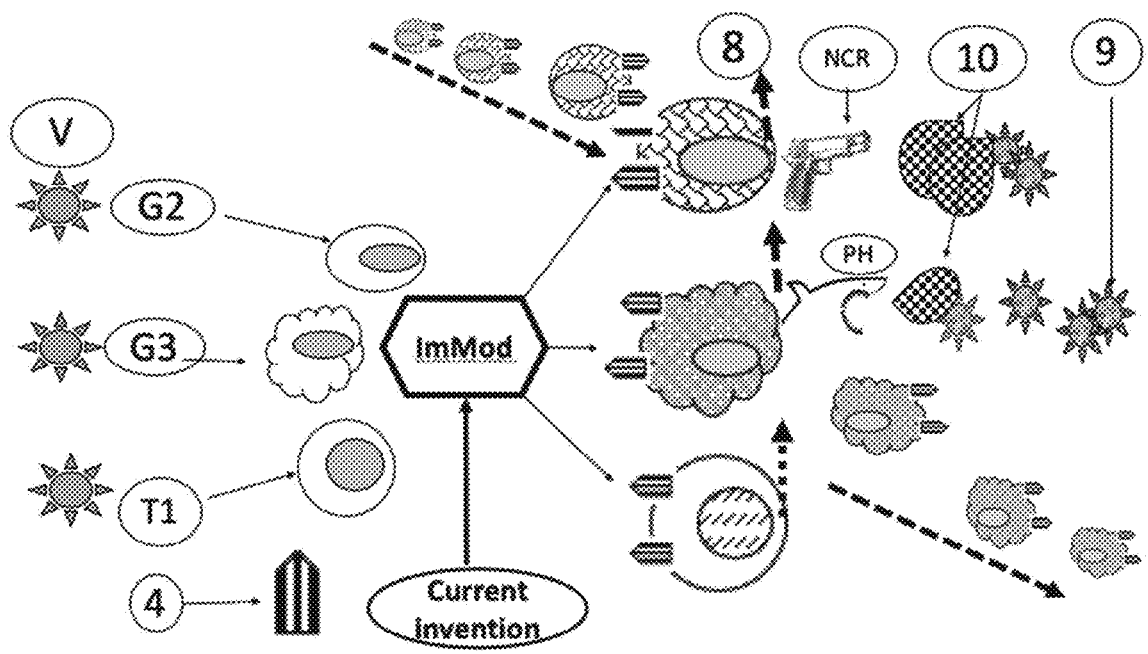
FIG. 2 demonstrate the proposed immunomodulatory mechanisms of *Nigella sativa* composition (ImMod) of this invention.
Figure 3:
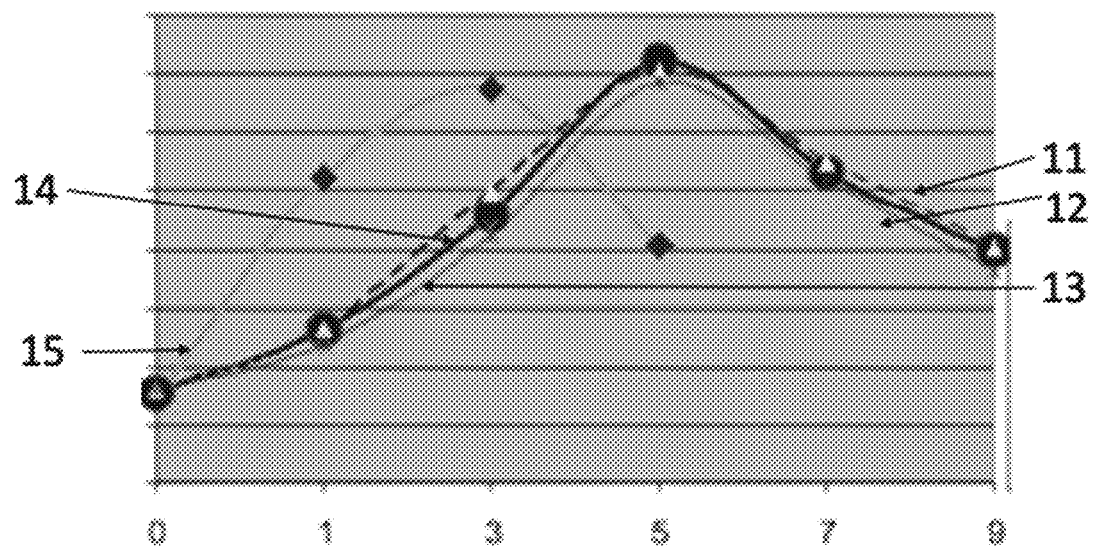
FIG. 3 demonstrate the BCG like activity of *Nigella Sativa* extracts.

Novel Acid Extraction/Bio-Fermentation Process of *Nigella Sativa* Seeds:

In this invention, the process of extraction of the bioactive phytochemical composition from *Nigella sativa* seeds consists of three steps of acid extraction of NS seeds; bio-fermentation of the extract; and incubation of the extract as a continuous process that take place over a period of time ranging from few hours to 40 days and beyond up to 1 year.

The solvent used for the extraction of NS seeds is Ethanoic acid (vinegar, carboxylic acid) in a range of concentration from 0.1% to 20%, preferably 1% to 5%, with or without the mother of vinegar, preferably with the mother of vinegar and incubation of the extract under aerobic or anaerobic conditions.

What are the chemicals that are being extracted by the novel process of this invention?

The chemical composition of *Nigella sativa* seeds has been extensively studied in published research. The seeds contain 20-85% of protein, 38.20% of fat, 7-94% of fiber, and 31.94% of total carbohydrates (Yimer et al., 2019).

According to Forouzanfar et al., (2014) To identify the composition of the *Nigella sativa* (NS) seeds sodium dodecyl sulfate polyacrylamide gel electrophoresis (SDS-PAGE) was used. The fractionation of whole NS seeds was done which shows the bands ranged from 94 to 100 kDa molecular mass and the results are as follows:

The fixed oil (32-40%) contains: unsaturated fatty acids which includes: arachidonic, eicosadienoic, linoleic, linolenic, oleic, almitoleic, palmitic, stearic and myristic acid as well as beta-sitosterol, cycloeucalenol, cycloartenol, sterol esters and sterol glucosides.

The volatile oil (0.4-0.45%) contains saturated fatty acids which includes: nigellone that is the only component of the carbonyl fraction of the oil, Thymoquinone (TQ), thymohydroquinone (THQ), dithymoquinone, thymol, carvacrol, α and β-pinene, d-limonene, d-citronellol, p-cymene volatile oil of the seed also contains: p-cymene, carvacrol, t-anethole, 4—terpineol and longifolene.

Total oil refers to a product that contains both fixed and volatile NS oil.

NS seed have two different forms of alkaloids: isoquinoline alkaloid that includes: nigellicimine, nigellicimine n-oxide and pyrazol alkaloid that includes: nigellidine and nigellicine. As an alkaloid, Nigellidine is soluble in acid media. Hence, it can be extracted with the current method using ethanoic acid. Nigellidine have not been extracted according to google search. Alkaloids form salts with acids, and those salts are water soluble. A solution of acetic acid in ethyl acetate may, possibly, be also effective for the acid extraction of the considered alkaloid (Wiki).

NS seeds also have saponin and alpha-hederin which is it is a triterpenoid saponin present in the defatted seeds of NS and is water soluble (El-Tahir and Bakeet, 2006; Wiki). Alpha-hederin have bronchiolytic pharmacologic action is related to symptoms of mucus, wheezing, shortness of breath and chest discomfort as symptoms of bronchitis or bronchial hypersensitivity and asthma. The anti-inflammatory effect of alpha-hederin is possibly through mediators synthesized by T-lymphocytes, endothelial cells through the IFN induced innate and adaptive immunity against viral and some bacterial infections (Muhammad, 2017).

Total synthesis of Nigellidine is described by Khan and Afzal, 2016, and synthesis of alpha-hederin is described by Plé et al., 2004.

Most of the pharmacological activity of the entire seed or their extract are mainly ascribed to its volatile oil, of which thymoquinone (2-isopropyl-5-methyl-1,4benzoquinone) is the most profuse component (Iqbal et al., 2018). Thymoquinone can be quantified using RP-HPLC and authentic standards of thymoquinone purchased from Sigma-Aldrich. One serious drawback with thymoquinone is its toxicity at high doses and poor water solubility which limit its usage as a therapeutic agent (Khan and Afzal, 2016).

The nutritional compositions of NS are vitamins, carbohydrates, mineral elements, fats and proteins that include eight or nine essential amino acids. Most of the pharmacological effects are due to quinine constituent, of which TQ is the mainly abundant. TQ possess antioxidant, anti-inflammatory, antibacterial and antifungal activity (Forouzanfar et al., 2014).

The seed have an intensely bitter taste due to the presence of a seed protein nigellin and bitter principle (Kalidasu et al., 2017), the oil and/or the solvent (Bornare et al., 2015).

Microscopical location of the bioactive phytochemicals of NS: The grey colored albumen consisting of thin-walled cells, with several oil droplets (Margout et al., 2013). The saponin α-hederin accumulate both in the seed coats and the inner seed tissues at different ratios (Botnick et al., 2012).

The most important compounds due to which medicinal value of these seeds increased are saponins, flavonoids, volatile oil. Phytochemical analysis of NS extracts is detailed by Amir et al., 2018).

According to Gholamnezhad et al., 2015 *Nigella sativa* Chemical compounds PubChem CID is the following Thymoquinone (PubChem CID: 10281), Dithymoquinone or Nigellone (PubChem CID: 398941), Thymol (PubChem CID: 6989), Carvacrol (PubChem CID: 10364), p-Cymene (PubChem CID: 7463), 4-Terpineol (PubChem CID: 11230), Trans-anethol (PubChem CLD: 637563), Alpha-pinene (PubChem CID: 6654), Alpha-hederin (PubChem CID. 71464054), Kaempferol glucoside (PubChem CID: 12358425).

Figure 4A:
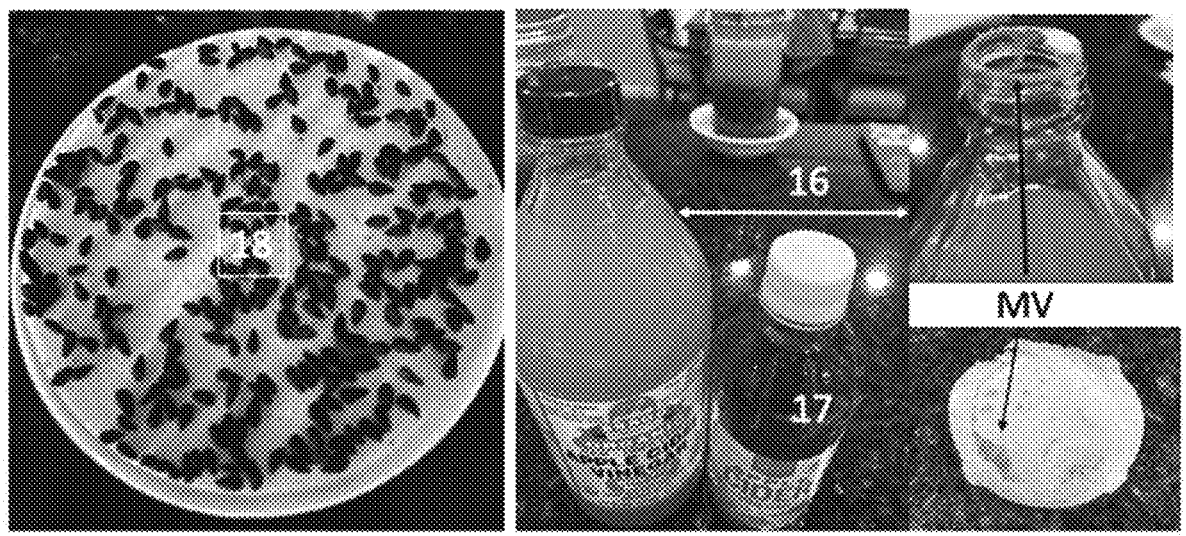
FIGS. 4A and 4B demonstrate the commercial vinegar used in the process of acid extraction of NS seeds and *Nigella sativa* dried seeds.

Material and Methods
Materials Used
1—In the acid extraction process of this invention carboxylic acids are used because they are organic acids, week and soluble in water. Carboxylic acids contain a functional group called the carboxylic group (—COOH), with a general formula $C_nH_{2n+1}COOH$ including 20 straight-chained saturated carboxylic acids and others (chemistry yolp website). By way of example, and for practical purposes acetic acids was selected because it is available commercially and it serves the purpose of safety for human consumption. The trivial name acetic acid is the most commonly used and preferred IUPAC name. The systematic name ethanoic acid, a valid IUPAC name, is constructed according to the substitutive nomenclature. The name acetic acid derives from acetum, the Latin word for vinegar, and is related to the word acid itself. Vinegar is an aqueous solution of acetic (ethanoic) acid and trace chemicals and flavors. Vinegar typically contains 5-8% acetic acid by volume. Usually the acetic acid is produced by the fermentation of ethanol or sugar by acetic acid bacteria. There are many types of vinegar, depending on source materials including fruit, palm, balsamic, cane, grains, spirit, white wine vinegar and the white distilled vinegar. FIG. 4A demonstrates the extraction solvent used is the commercially available raw apple cider vinegar (16), purchased from local groceries. The solvent has a concentration of ethanoic acid in water 5% acidity. The vinegar is either raw unfiltered with the "mother of vinegar" in an amount of about %-1 cubic centimeters per liter of vinegar, or it is filtered and pasteurized without a mother of vinegar. The vinegar acidity of both raw and filtered is 5% acidity as it is diluted in water. The raw apple cider vinegar used in the experiment is of 3 Trade names: Bragg, Nature Intent and Simple Truth. The filtered pasteurized apple cider vinegar is Trade named Market Pantry (17). Ethanoic acid, also known as acetic acid, is one of the carboxylic acids. Ethanoic acid is a liquid organic compound with the chemical formula $CH_3COOH$. It is colorless with sharp acrid smell.

The "mother of vinegar" that is present in the commercially available 1-liter vinegar bottle (MV) is a brownish sedimented powder about ½-1 $CC^3$ in volume, that settles on the bottom of the container. The vinegar can be stored for months without any detectable changes, activity or multiplication of this mother of vinegar.

The raw apple cider vinegar is mostly apple juice, but adding yeast turns the sugar in the juice into alcohol. This is a process called fermentation. Bacteria turn the alcohol into acetic acid. That's what gives vinegar its sour taste and strong smell, i.e., the raw unpasteurized unfiltered apple cider vinegar contains both yeast and acetic acid bacteria.

2—*Nigella* is a genus of 18 species of annual plants in the family Ranunculaceae, native to Middle East, South Asia, North Africa, Southern Europe and Southwest Asia. Common names applied to members of this genus are caraway, *Nigella*, black seed and black cumin, Kala Jeera, Cumin Noir. In this invention and by the way of example we will refer to *Nigella sativa* because it is available and is safe for human consumption.

*Nigella sativa* (NS) is an annual flowering plant in the family Ranunculaceae. The plant grows to 20-30 cm tall, with finally divided linear leaves. The flowers are delicate, and usually colored pale blue and white. The fruit is a large and inflated capsule composed of three to seven united follicles, each containing numerous seeds which are used as a spice and folklore medicine. The genus name *Nigella* is a diminutive of the Latin niger (black), referring to the seed color.

Any part of the plant can be extracted for its bioactive phytochemicals of this invention, preferably the seeds of *Nigella sativa*.

*Nigella sativa* L. is classified by the United States Department of Agriculture (USDA) in the buttercup family—Ranunculaceae, genus *Nigella* L. and species *Nigella sativa* L.—Black cumin.

Pharmaceutical Name: Semen *Nigellae sativae*.

Other names: black caraway, *Nigella*, black cumin kalojeera, kalonji or kalanji, Habat al-baraka, Ketash, Schwarz kummel, and 'Hak Jung Chou' and many others.

Figure 4B:

In the following discussion the name *Nigella sativa* or NS are being used alternatively. FIGS. 4A and 4B demonstrate *Nigella sativa* dried seeds (18) purchased from local grocery stores under the Trade name Sadaf (www.sadaf.com), Azure (www.westcoastpita.com), Al Attar Spices, Crescent, online black seed purchased under the Trade name Terrasoul Superfood, Adonis and Deep (depicted in FIG. 4B). All the NS seeds are packed in the USA. NS seeds are used without any further treatment.

Figure 5:
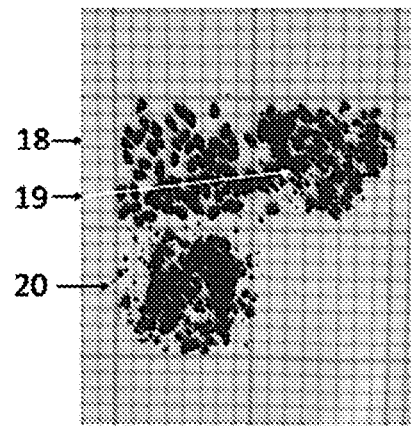
FIG. 5 depicts grinding sizes of NS seeds.

FIG. 5 depicts grinding sizes of NS seeds including coarsely grinded seed (19) and finely grinded seed (20) placed on a graph paper to compare the grind size to the whole seed (18)

3—Spring water (21) Trade named Crystal geyser that have a total mineral contains of 90 mg/liter, including: sodium 13 mg, potassium 2 mg, calcium 27 mg, magnesium 6 mg, sulfate 36 mg, chloride 6 mg. Distilled water can be used.

4—*Nigella sativa* cold-pressed oil Trade named Hemani (Kalonji, Black Seed oil) (www.haemanitrading.ae).

5—Olive oil as control

Equipment Used

Figure 6:
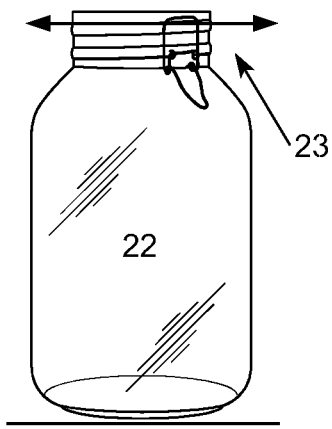
FIG. 6 demonstrate the glass jar, the container in which the process of NS seed extraction is taking place.

1—FIG. 6 demonstrate the glass jars or container (22) in which the process of solvent/seed interaction to form the bioactive phytochemical therapeutic composition is taking place. The glass jar (22) have a lid that can clamp down on foods with vulcanized rubber gaskets (23) for an airtight seal. The container and can be filled to the top (arrowed) for anaerobic bio-fermentation of NS seeds. Different sizes of glass jars were used including a large jar volume is 1 gallon and a small jar volume is 1 liter.

2—Domestic spice grinder, electric, high speed, or any grinder known in the art.

3—Glass stirring rods.

4—PH Indicator Strips Trade named Oakton with 1.0 interval. Reading on a scale on 1-14, where a PH value of a neutral solution is 7.0. Solutions with PH value below 7.0 are considered acidic.

Experimental Design of Extracting *Nigella sativa* Seeds using Ethanoic Acid

The experimental variables included in the design are:
1. Seed type: using 6 locally available NS seeds and online available seeds packed in the USA.
2. Seed grind size: including whole seed, coarse grind, fine grind, crushed seeds and powder.
3. Solvent type: using 3 locally available ethanoic acid (vinegar) either unfiltered unpasteurized with the mother of vinegar (16) or pasteurized without the mother of vinegar (17).
4. Solvent dilution: in a range from 0.1% to 20%, preferably 5%, 1.66 or 1.25% diluted in mineral spring water (21) or distilled water.
5. Seed to solvent ratio: measured as weight/volume, using a range of different ratios.
6. The availability of oxygen: with either experiments being performed in an anaerobic condition with vulcanized rubber gaskets (23) for an airtight seal or under aerobic condition.
7. Bio-fermentation of the composition: by the effect of the presence of the mother of vinegar (MV), i.e., acetic acid bacteria observed from day 1 until day 40 and beyond up to 1 year.
8. The effect of incubation time on the composition: starting from few hours, to few weeks, to 40 days up to 1 year.

Why Selecting Ethanoic Acid?

There are several unique features of ethanoic acid as a solvent over prior art solvents. Theoretically speaking, ethanoic acid can produce different effects, not simple extraction, for example, but not limited to:
a. Ethanoic acid is a powerful polar solvent, although it is considered as a weak acid, but actually ethanoic acid is still a powerful polar organic solvent, that dissociates about 10^11 times more than ethanol, and is stronger than methanol.
b. Commercially available ethanoic acid in vinegar is diluted in water (5% acidity), therefore it has the advantage of an aqueous extraction in acid medium. Aqueous solution id ideal to dissolve the saponin alpha-hederin from NS seeds
c. Commercially available ethanoic acid (vinegar) (16) contains *Acetobacter aceti* (mother of vinegar) (MV) that will produce a bio-fermentation process during the incubation of the composition.
d. Ethanoic acid can expand and loosen the plant cell wall cellulose for a better extraction of intracellular phytochemicals.
e. Ethanoic acid is a safe solvent for human consumption; there is no need to use excessive heat to remove it, that could have a deleterious impact on the composition.
f. Ethanoic acid does not leave undesirable smell or taste in the composition.
g. Ethanoic acid does not extract the undesirable black pigment.
h. Vinegar act as a preservative for the composition that keep it stable for long time.

Step-by-Step Acid Extraction; Bio-Fermentation; and Incubation of *Nigella sativa* Seed of this Invention The steps for the preparation of NS extract in acid solvent and bio-fermentation of the extract include: select the type of NS seeds and vinegar as the starting material; grinding the seed; place the NS seeds in a container; soak NS seeds in ethanoic acid solvent for few hours; fill up the container with either ethanoic acid or water (21) to reach the desired acidity % of the composition; close the container under either anaerobic or aerobic conditions; incubate the composition at room temperature under either daylight or dark room; produce a composition ready for use as a therapeutic agent either within few hours or after incubation over days, weeks up to 40 days and beyond up to 1 year to allow time for the bio-fermentation process.

FIGS. 4A-4B demonstrate the 2 starting materials: First, a solvent ethanoic acid present in apple cider vinegar solutions 5% acidity with the mother of vinegar that is raw unpasteurized and unfiltered (16) or pasteurized without the mother of vinegar (17). Second, *Nigella sativa* Linn dry herbal seeds (18).

FIG. 5 demonstrates whole NS seeds (18) coarse grinded NS seeds (19) and fine grinded NS seeds (20) used in this process.

Grinding *Nigella* dried seeds: A small electric coffee grinder was used to chop up the NS seeds (18). Small batches of the seed were grinded, approximately 50 grams each time.

Fine grind: For the fine grind, the *Nigella* seeds were chopped up for 20 seconds (19).

Coarse grind: For the coarse grind, the *Nigella* seeds were chopped up for 10-15 seconds (20).

Powdered NS seed: For the powder, the *Nigella* seeds were chopped up for 30 seconds.

The time between grinding and the use of the seed is variable. Crushed or flaked NS seed can also be used.

Figure 7:
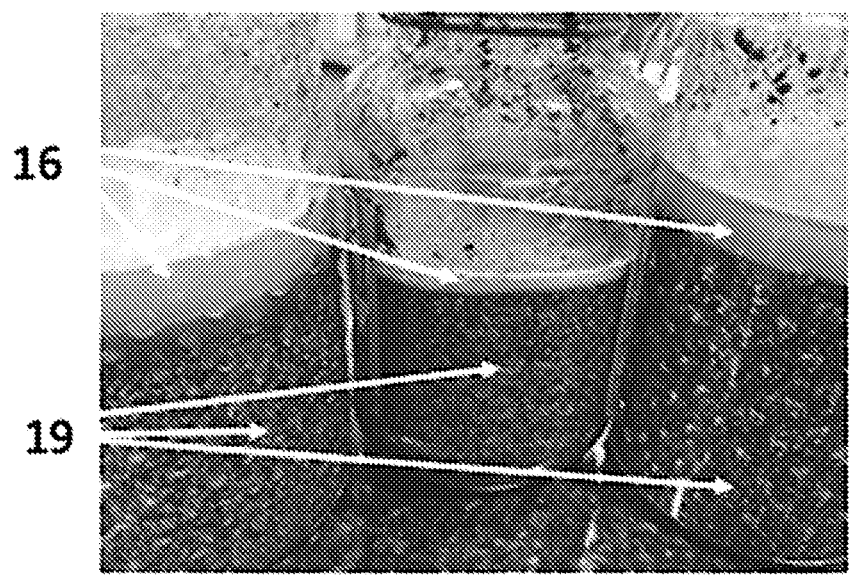
FIG. 7 demonstrate the first step of acid extraction/bio-fermentation: soaking of NS seeds.

FIG. 7 demonstrate soaking NS seeds: Place 200-grams of grinded NS seeds in 1—liter glass container (22); add ½ liter of 5% ethanoic acid with the mother of vinegar (16); mix the content manually using a glass stirring rod. The grinded seeds are left to soak in the solvent for 2-8 hours preferably 4-hour period at room temperature. During the soaking time, the contents are mixed manually 4-8 times, using a glass stirring rod until the seed absorb almost all the solvent.

After the NS seeds absorb most of the solvent, "fill up" the container to the top by adding ethanoic acid 5%. The final concentration of the solvent is 5% acidity. Close the container airtight with its lid that contains the rubber vulcanized gasket (23) to generate an anaerobic environment.

Incubate the mixture at room temperature either in daylight or in dark room.

The composition is incubated over a period of either 8-24 hours, or few days up to 40 days and beyond up to 1 year.

Observations were made at frequent intervals for changes in the physical characteristics.

Figure 8:
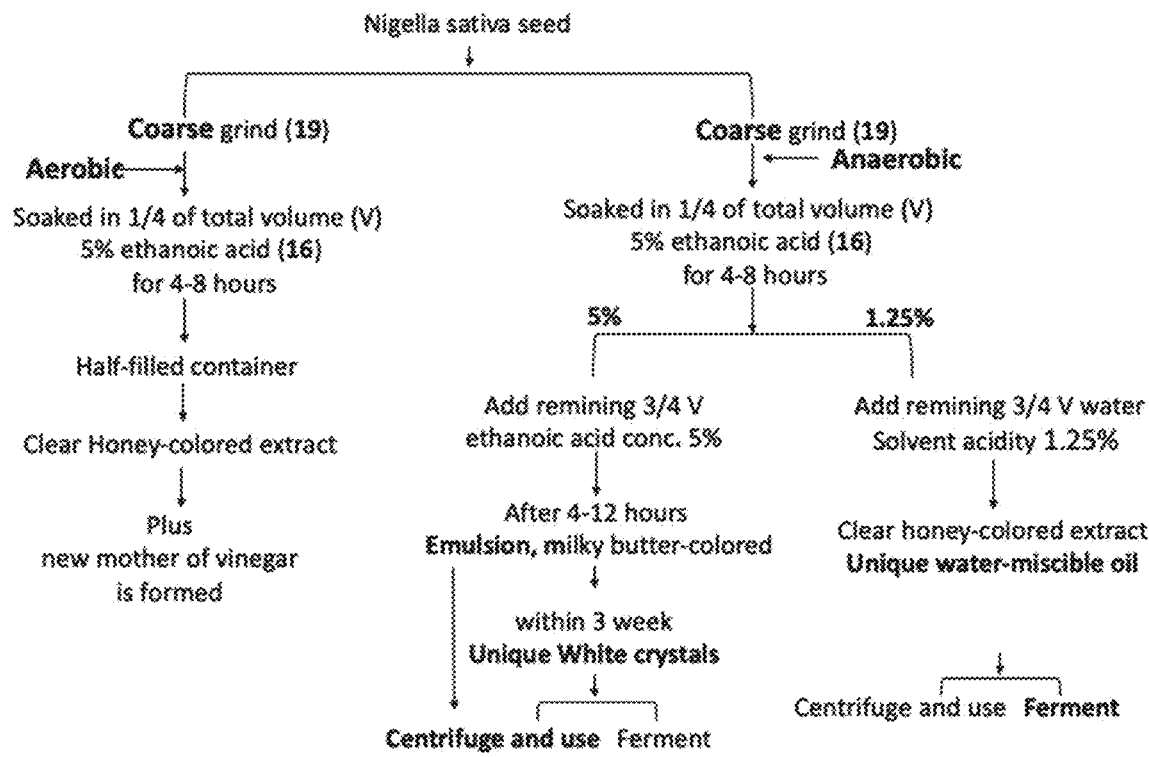
FIG. 8 demonstrate a flow chart of the process of extraction of coarsely grinded NS seeds in different acidity of ethanoic acid solvent with the mother of vinegar.
Figure 9:
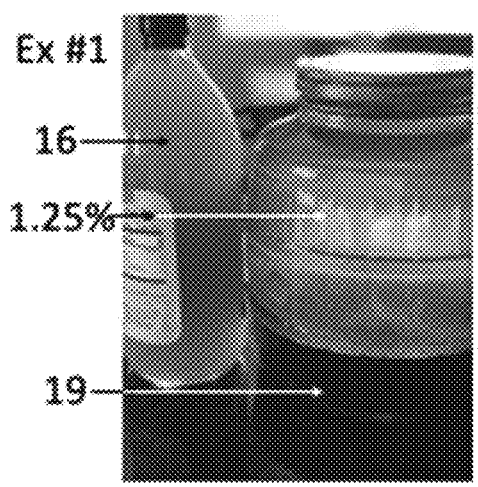
FIG. 9 demonstrate example #1, that depicts a jar that contains a composition of coarsely grinded NS seed in 1.25% ethanoic acid with mother of vinegar, under anaerobic condition.

FIG. 8 is a flow chart demonstrating in the right side, the process of extraction of coarsely grinded NS seeds (19) in ethanoic acid solvent with the mother of vinegar (16) in either 1.25% or 5% solvent acidity, and describes the physical characteristics of the extract (product) wherein NS seeds are under the effect of the acid solvent and the bio-fermentation, and the duration of incubation needed to have the bioactive phytochemical composition ready for use. The left side describes that ethanoic acid extraction as being conducted using ethanoic acid without the mother of vinegar (17) to get similar physical characteristics of the composition. The flow chart of FIG. 8 is further explained by the way of examples:

FIG. 9 demonstrate example #1: that depicts a coarsely grinded NS seed (19) in ethanoic acid with mother of vinegar (16) with 1.25% acidity, under anaerobic condition. In one embodiment, the coarsely grinded seeds are soaked in ethanoic acid solvent 5% acidity in an amount that is ¼ of the total container volume for 4 hours; further, the container is filled to the top with spring water (21), the final solvent acidity is 1.25%; the contents are mixed and the container is closed airtight to generate anaerobic conditions. The mixture is incubated at room temperature either in daylight or in dark room. The composition is incubated over a period of either 8-24 hours, or few days up to 40 days and beyond up to 1 year to determine the physical changes that results from ethanoic acid extraction and bio-fermentation of the composition as a result of the presence of the mother of vinegar (MV).

Figure 10:
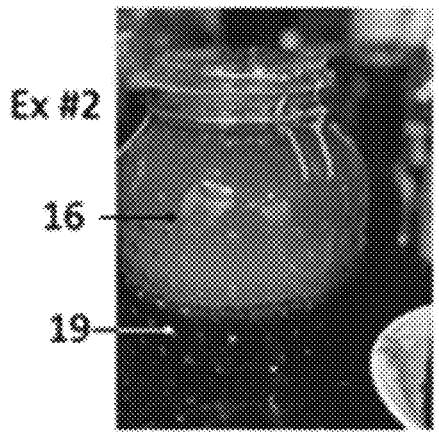
FIG. 10 demonstrate Example #2, that depict a jar that contains a composition of coarsely grinded NS seed in 5% ethanoic acid acidity with the mother of vinegar, under anaerobic conditions.

FIG. 10 demonstrate Example #2 that depict a coarsely grinded NS seed (19) in ethanoic acid with the mother of vinegar (16) with 5% acidity under anaerobic conditions.

Figure 11:
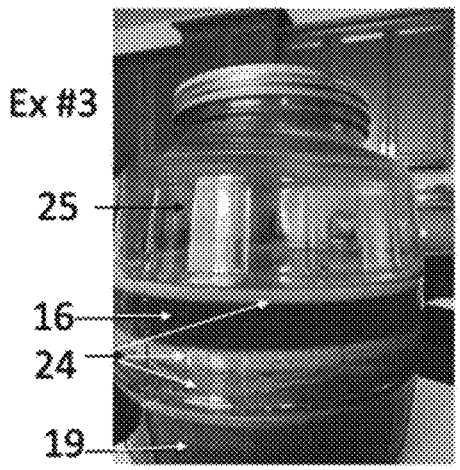
FIG. 11 demonstrate Example #3, that depict the process of extraction of coarsely grinded NS seeds in 5% ethanoic acid, under aerobic condition with the formation of thick multi-layered new mother of *Nigella sativa*.

FIG. 11 demonstrate Example #3 that depict the process of extraction of NS seeds under "aerobic" condition described in the left side of the flow chart (FIG. 8) wherein coarsely grinded NS seeds (19) placed in a 4-liter glass container (22) and 1-liter of acetic acid 5% acidity with mother of vinegar (16) is added (volume of ¼ of the container); soaked for 4-8 hours; further 1-liter of acetic acid solvent 5% (16) is added to fill ½ the container, leaving the upper half filled with air (25). The container is half-filled to generate aerobic conditions for ethanoic acid extraction of the bioactive phytochemicals from NS seeds and/or bio-fermentation with growth of new "mother of Nigella sativa (24) for the purpose of this invention.

Note: The variation in the size of the containers have no significance.

Figure 12:
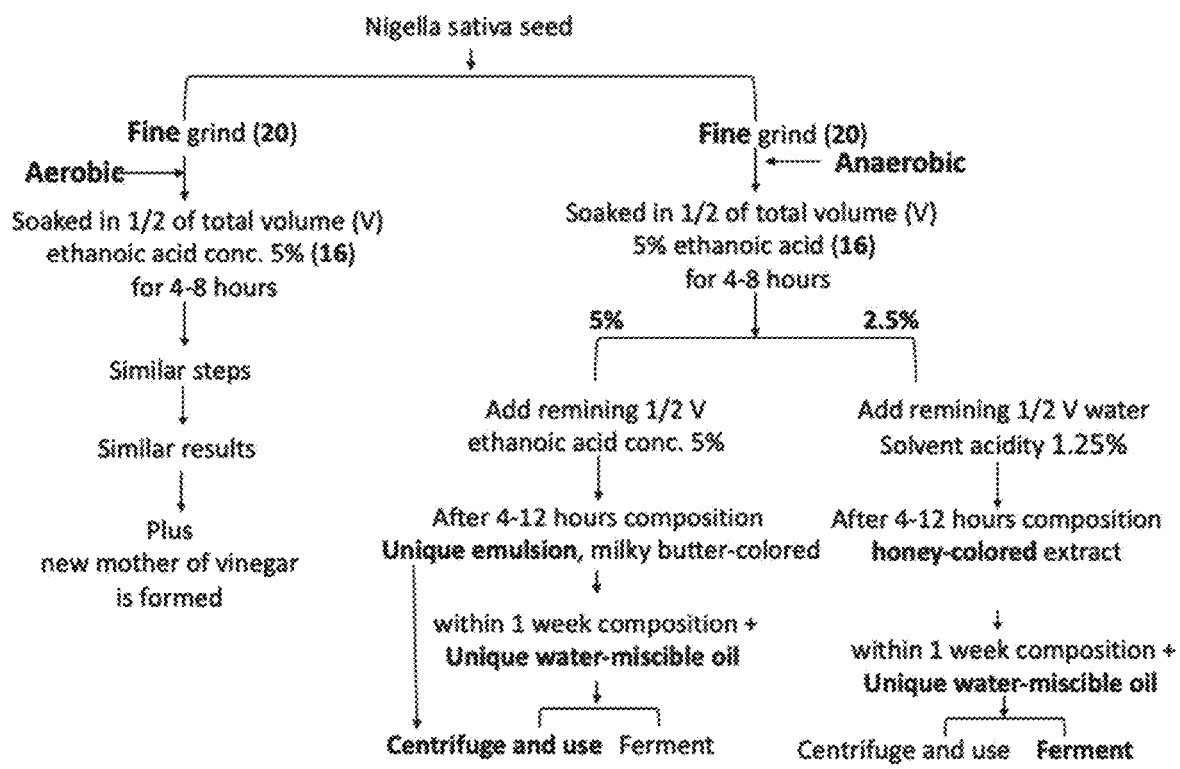
FIG. 12 is a flow chart demonstrating the process of extraction of finely grinded NS seeds in ethanoic acid solvent in different acidity with the mother of vinegar.

FIG. 12 is a flow chart demonstrating in the right side, the process of extraction of finely grinded NS seeds (20) in ethanoic acid solvent with the mother of vinegar (16) in either 1.25% or 5% solvent acidity, and describes the physical characteristics of the extract (product) wherein NS seeds are under the effect of the acid solvent and the bio-fermentation, and the duration of incubation needed to have the bioactive phytochemical composition ready for use. The left side describes that ethanoic acid extraction is being conducted without the mother of vinegar (17) to get similar physical characteristics of the composition. The flow chart of FIG. 12 is further explained by the way of examples:

FIG. 13 demonstrate example #4: that depicts a jar contains a composition finely grinded NS seed (20) in ethanoic acid with mother of vinegar (16) with 2.5% acidity, under anaerobic condition. In one embodiment, the finely grinded seeds (20) are soaked in ethanoic acid solvent 5% acidity in an amount that is ½ of the total container volume for 4-8 hours; further, the container is filled to the top with spring water (21), the final solvent acidity is 2.5%; the contents are mixed and the container is closed airtight to generate anaerobic conditions. The mixture is incubated at room temperature either in daylight or in dark room. The composition is incubated over a period of either 8-24 hours, or few days up to 40 days and beyond up to 1 year to determine the physical changes that results from ethanoic acid extraction and bio-fermentation of the composition.

FIG. 14A demonstrate example #5: that depicts a jar that contains a composition of finely grinded NS seed (20) in ethanoic acid with mother of vinegar (16) with 5% acidity, under anaerobic condition. In one embodiment, the finely grinded seeds (20) are soaked in ethanoic acid solvent 5% acidity in an amount that is ½ of the total container volume for 4-8 hours; further, the container is filled to the top with ethanoic acid 5% (16), the final solvent acidity is 5%; the contents are mixed and the container is closed airtight to generate anaerobic conditions. The mixture is incubated at room temperature either in daylight or in dark room. The composition is incubated over a period of either 8-24 hours, or few days up to 40 days and beyond up to 1 year to determine the physical changes that results from ethanoic acid extraction and bio-fermentation of the composition.

FIG. 14B demonstrate the appearance of a drop of the emulsion of example #4 on a table top (E). The emulsion (E) is thick and homogenous milky with a pale-yellow color that is quite different from the starting materials.

Figure 15:
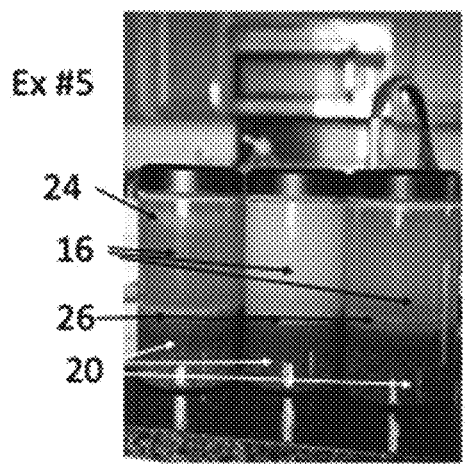
FIG. 15 demonstrate example #6, that depicts reproducibility of the composition of finely grinded NS seed in 5% ethanoic acid with mother of vinegar, under aerobic condition (the lid is not airtight), the new mother of NS and the layering of the composition particularly the white layer.

FIG. 15 demonstrate example #6: that depicts a group of three jars that contains a composition of finely grinded NS seed (20) in ethanoic acid with mother of vinegar (16) with 5% acidity, under aerobic condition (the lid is not airtight). In one embodiment, the finely grinded seeds (20) are soaked in ethanoic acid solvent 5% acidity in an amount that is ½ of the total container volume for 4-8 hours; further, the container is filled to the top with ethanoic acid 5% (16), the final solvent acidity is 5%; the contents are mixed and the container is closed under aerobic conditions.

The mixture is incubated at room temperature either in daylight or in dark room. The composition is incubated over a period of either 8-24 hours, or few days up to 40 days and beyond up to 1 year to determine the physical changes that results from ethanoic acid extraction and bio-fermentation of the composition.

FIG. 15 shows a thick new mother of Nigella sativa (24) over the whole mouth of the container. The mother of Nigella sativa consists of strands of proteins, enzymes, and friendly bacteria.

Figure 16:
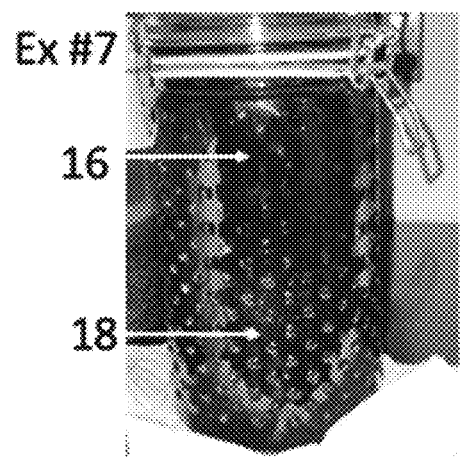
FIG. 16 demonstrate example #7, wherein the whole seed is extracted in 5% ethanoic acid with the mother of vinegar.

FIG. 16 demonstrate example #7 wherein the whole seed (18) is extracted in ethanoic acid with the mother of vinegar (16) 5% acidity. The disadvantage of this method is that large amount of the black pigment is extracted and there is minimal oil extraction.

In one embodiment, NS seed is extracted with water; and mother of vinegar (MV) is added to NS aqueous solution and the composition incubated at room temperature for days, weeks up to 40 day and beyond to get a fermented NS seed product.

In one embodiment, the solvent used in the process or comprised in the product advantageously comprises other elements such as alkali or alkaline metals including sodium, potassium, magnesium or combination of any of the above that facilitate the chemical and physical changes in the composition.

In one embodiment, the solvent used in the process and/or comprised in the product advantageously comprises other elements such as sulfur, nitrogen, carbon, and oxygen. There elements can be present as sulfides, sulfates, nitrates, and/or carbonates or combination of any of the above that facilitate the chemical and physical changes in the composition.

Table 2 provides further details of the NS extraction experimental variables and outcomes. Table 2 include 26 samples distributed among 7 experiments. The 26 experiments are testing the interaction between the experimental variables included in the design of the extraction process. The examples are not a limiting factor of the extraction process.

The experimental variables included in the design, as demonstrated in table 2, include the Trade names of the seed and solvent used, the seed grind size, the solvent acidity %, the quantity of each, seed/solvent ratio and how many cubic centimeters (CC) are equivalent to 1-gm of the seed, the date of the preparation, the extract characteristics, with unique observations on the experimental outcomes. Table 2 also provide reference to which sample is included under which experiment number.

TABLE 2

| No | Seed & solvent Tradenames | Grind size | Acid dilution | 1 gm seed in cc composition | Date | Extract characters | Unique observations and PURE compounds | Example number |
|---|---|---|---|---|---|---|---|---|
| 1 | Sadaf and Simple Truth | Coarse | 1.25% | 240 gm/4 L (1 gm in16.6 cc) | 03/19 | Clear, transparent, honey-yellow | Floaters | Example #1 |
| 2 | Sadaf and Bragg | Coarse | 1.25% | 240 gm/4 L (1 gm in16.6 cc) | 03/19 | Same as #1 | Gas bubbles large amount with bubbling sound: photos in 04/21till 05/28 | Example #1 |
| 3 | Sadaf and Bragg | Coarse | 1.25% | 340 gm/4 L (1 gm in 11.8 cc) | 03/19 | Same as #1 | | Example #1 |
| 4 | Sadaf and Simple Truth | Coarse | 1.25% | 340/4 L (1 gm in 11.8 cc) | 03/19 | Same as #1 | | Example #1 |
| 5 | Azure and Nature Intent | coarse | 1.25% | 600 gm/4 L (1 gm in 6.6 cc) | 03/19 | Same as #1 | Gas bubbles | Example #1 |
| 6 | AL attar and Nature Intent | coarse | 1.66% | 228 gm/3 L (1 gm in 13 cc) | 03/29 | Same as #1 | | Example #1 |
| 7 | AL attar and Nature Intent | coarse | 1.66% | 228 gm/3 L (1 gm in 13 cc) | 03/29 | Same as #1 | | Example #1 |
| 8 | Crescent and Bragg | Coarse | 5% | 400 gm/3 L (1 gm in 7.5 cc) | 04/22 | Emulsion, semi-opaque milky | Unique pure white crystalized salt Floaters Transform | Example #2 |
| 9 | Crescent and Bragg | coarse | 5% | 400/3 L 1 gm in 7.5 cc | 05/21 | Emulsion, semi-opaque milky | DUPLICATE # 8 | Example #2 |
| 10 | Terrasoul | coarse | 5% | 400 gm/2 L (1 gm in 5 cc) | 03/29 | Transparent honey color | Aerobic, New NS mother | Example #3 |
| 11 | Azure and Bragg | Fine | 5% | 200 gm/1 L (1 gm in 5 cc) | 04/03 | Emulsion, semi-opaque, milky | Transform | Ex #4 |
| 12 | Azure and Bragg | Fine | 5% | 200 gm/1 L 1 gm in 5 cc | 04/03 | Emulsion, semi-opaque, milky | Transform from opaque to semi-opaque | Ex #4 |
| 13 | Crescent and Bragg | Fine | 5% | 200 gm/1 L 1 gm in 5 cc | 04/03 | Emulsion, opaque milky | No transformation, sticky, biter when conc. | Example #4 |
| 14 | Azure | Fine | 5% | 300gm/1.5L (1 gm in 5 cc) | | Emulsion, semi-opaque, milky | Transform | Example #4 |
| 15 | Azure and Simple Truth | Fine | 5% | 200 gm/1 L 1 gm in 5 cc | April 1 | Emulsion, opaque milky | No Transformation | Example #4 |
| 16 | Sadaf and Bragg | Fine | 5% | 225 gm/1.7 L (1 gm in 7.5 cc) | 04/19 | Emulsion, semi-opaque, milky | Transform, New NS mother | Example #5 |
| 17 | Crescent and Brag | Fine | 5% | 225 gm/1.7 L (1 gm in 7.5 cc) | | Emulsion, opaque milky | No Transformation | Example #5 |
| 18 | Adonis and Bragg | Fine | 5% | 225/1.7 L (1 gm in 7.5 cc) | | Emulsion, semi-opaque, milky | Transform, New NS mother | Example #5 |

TABLE 2-continued

| Seed & solvent No Tradenames | Grind size | Acid dilution | 1 gm seed in cc composition | Date | Extract characters | Unique observations and PURE compounds | Example number |
|---|---|---|---|---|---|---|---|
| 19 Azure | Fine | 2.5% | 200 gm/1 L (1 gm in 5 cc) | | Transparent blackish | | Example #6 |
| 22 Crescent | Whole seed | 5% | 200/1 L (1 gm in 5 cc) | 05/15 | Transparent deep black colored | Gas bubbles 1st day only | Example #7 |
| 21 Commercial Oil and Bragg | oil | 5% | | | | Pure novel oil drops in solvent | Example #8 |
| 22 crescent | Whole seed | water | 200/1 L (1 gm in 5 cc) | 04/22 | Deep-colored blackish | Gone bad; add preservative | |
| 23 Azure | Fine | water | 200/1 L (1 gm in 5 cc) | 04/22 | Deep-colored blackish | Gone bad; add preservative | |
| 24 Sadaf | Coarse | water | 225/1 L (1 gm in 4.4 cc) | 04/22 | Deep-colored blackish | Gone bad; add preservative | |
| 25 Sadaf | Coarse | 10% | 200/1 L | 04/22 | Milky | Irritant Aroma | |
| 26 Azure | Fine | 15% | 200/ml | 04/22 | Milky | Irritant Aroma | |

Note:
the NS weight and ethanoic acid volume and % acidity can vary slightly.

The NS Pulp

In one embodiment, the residual NS seed pulp is further used pressed to extract the liquid content using methods known in the art; the extracted liquid can be added to the composition or used separately.

In other embodiments, the residual pulp is re-extracted and re-fermented.

In other embodiment, the residual pulp is used in animal feed or plant soil.

Experimental Results:

Changes in the Physical Properties

Experimental Results of Acid Extraction/bio-fermentation process of *Nigella sativa* Seed The results of extracting the bioactive phytochemical composition from NS seeds using ethanoic acid in different concentrations with or without the mother of vinegar (MV) have been described under FIGS. 8-16; detailed in table 2. Most of the physiochemical properties of the bioactive phytochemical composition of NS in ethanoic acid were assessed by visual observations. The immediate changes in the physical properties of the novel composition as compared to the starting materials (solvent and the NS seed) was observed and recorded during the first day of mixing. Later, the gradual changes of the physical properties in the resultant composition were observed and recorded on daily and weekly intervals. The physiochemical properties of the composition are described under the following topics:

A—The effect of different variables on the outcomes, the most significant variables are:

Ethanoic acid concentration (% acidity), wherein an acidity of 5% resulted in an opaque pale-yellow emulsion. the light is absorbed, and is not allowed to pass by the particles present in the solution including water miscible oil, protein, cell structure and other particles as depicted in FIGS. 14A and 14B. On the other hand, an acidity less than 5% resulted in a honey-colored, clear, homogeneous mixture that contains many solutes extracted from NS bioactive phytochemicals in ethanoic acid as a solvent, the composition is only of one phase, no black pigment is extracted into this composition, the composition is optically transparent, allowing much of the day light that falls on them to be transmitted through the material with a brilliant shining color as depicted in FIG. 9.

NS seed grind size, wherein the finer the grind size the higher the concentration of the composition as judged by the depth of the color, and a thicker emulsion obtained.

Availability of oxygen for bio-fermentation, wherein an airtight container with a vulcanized rubber gasket produce either no or minimal new NS mother (24 of FIGS. 11 and 15)) formation while availability of oxygen, even to the minimum amount allows the development of thick (0.1-5 cm thick), multi-layered new NS mother as shown in FIG. 11 (24).

The presence of the mother of vinegar (FIGS. 11 and 15) that initiate a "dynamic" process of fermentation and all the subsequent changes in the composition and the formation of new NS mother that can be used as a complimentary therapy versus the absence of the mother of vinegar that resulted in a "static" acid extraction on NS seeds.

The seed/solvent ratio affect the concentration of the solutes within the composition and is visualized by the depth of the honey-colored extract; the higher the ratio the deeper the color.

The seed and solvent type also affect the resultant composition, as some seed have higher extraction of oil and some seeds flocculate heavier than the others in concentrated solvent.

The duration of incubation is vital factor that allows for the effect of bio-fermentation and for the changes that results herewith.

B—Timewise observations on the outcomes of mixing NS and ethanoic acid:

Immediate results, that are seen within few hours of mixing, wherein, the composition is classified into either clear, honey-colored composition (FIG. 9, 11) or an opaque, milky pale-yellow colored composition (FIG. 14A, 14B, 15). This immediate result is believed to be dependent on the % acidity of the solvent. It is noticeable that the composition consists of a solute that is completely dispersed throughout the solvent. The total volume of the mixture in the jar is fixed. The composition resulted from extraction of NS seeds using ethanoic acid solvent is very much different than the starting material.

Figure 17:
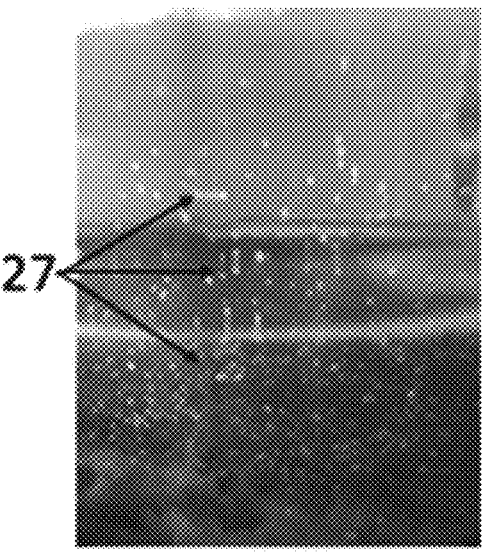
FIG. 17 depicts gas bubbles that are liberated during the process of bio-fermentation in acid medium.

Delayed onset result that are the outcomes of bio-fermentations including the liberation of gas bubbles and the formation of a new NS mother (24) that are seen within few days up to 40 days and beyond up to 1 year indicating the activity of bio-fermentation that is continuously going-on within the composition. Wherein gas bubbles are either continuously produced and can be seen whenever the jar is moved as depicted in FIG. 17 (27) over period of 4-7 weeks or at the time of soaking the seeds. Wherein, thick multi-layered new NS mother (24) is formed as seen in FIG. 11 and at the top of the composition or on the mouth of the container as seen in FIG. 18A (24). In the anaerobic container a thin new NS mother is formed as seen in FIG. 18B (24). Bio-fermentation is linked to the availability of oxygen and it results in the formation of a new thick new NS mother; this indicate that the composition keeps the acetic acid bacteria viable, provide the necessary food and oxygen for multiplication. will have effective bioactive phytochemical ingredients such as those discussed in the prior art. The "mother" is described as molecules of organic acids and enzymes connected in strand-like chains" that contain acetic acid bacteria (*Acetobacter aceti*).

Stability over-time of the composition, wherein, incubating the composition for 40 days and beyond up to 1 year at room temperature and day light make no changes in the physical characteristics of the composition including color, clarity and opacity, aroma, taste and preservation.

Figure 20:
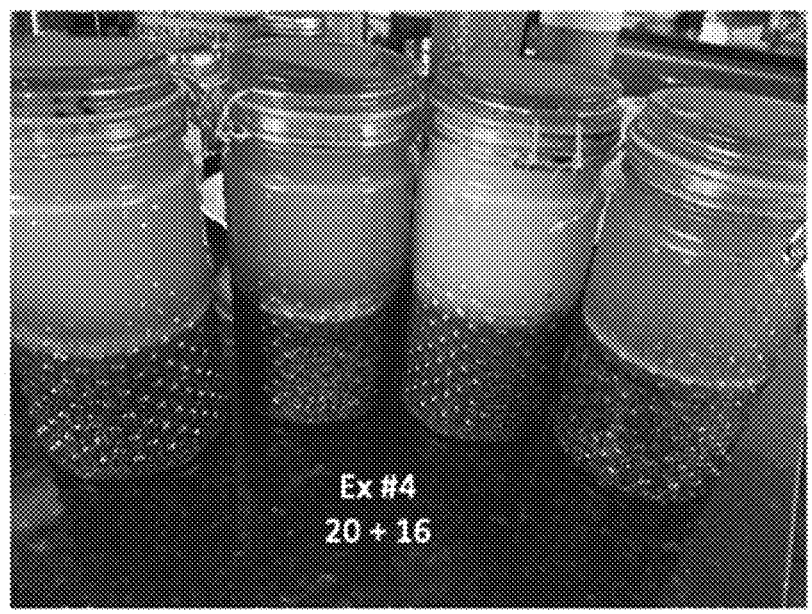
FIG. 20 depicts reproducibility of the type of the composition of finely-grinded NS in 1.25% ethanoic acid of Exp. #4.
Figure 21:
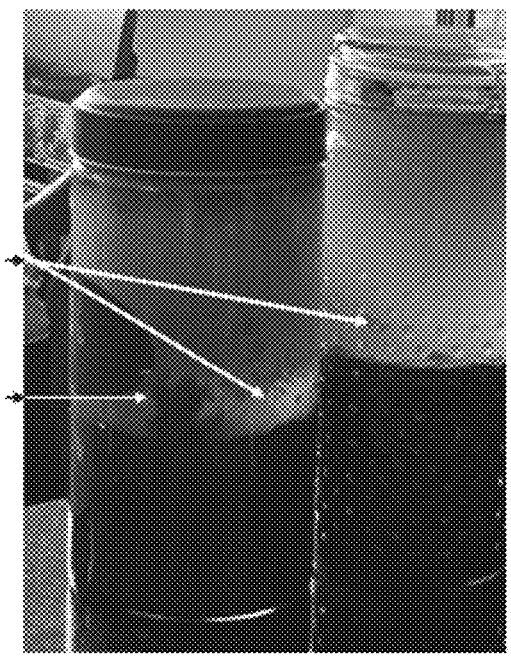
FIG. 21 depict two jars in which the composition appears to have two liquid phases with different color and different opacity: the emulsion above and the transparent below.

Layering of the composition as time passes, in addition to the black pulp on the bottom, and the composition appears to have two liquid phases with different color and different opacity. is happening over time as a result of precipitation, fermentation and conversion. Two new layers are being formed a white layer and a transparent layer. Wherein, the white layer seen in FIG. 15 (26) is present in almost all the jars, formed within 7-12 days, which is about 1-cm thick that is formed when the fine particles (Grinded NS or mother) floating in the suspension settles down. Wherein, the transparent layer is described as "zone of transformation" from opaque to semi-opaque phase as seen in FIGS. 21 and 20 (28), wherein, the lowest part of the composition that lies in contact with the white layer (26) make a dramatic change; allowing light to pass through and changes its phase, appearance, and character in this particular location of the composition. wherein, this change in the liquid phase is possibly due to a bio-fermentation process!

C—Reproducibility of the type of the composition: reproducible results refers to changes in the physical properties that are capable of close imitation of each other, can be made again each time in different experiments in multiple containers where the solvent and NS seeds were treated as in the flow chart. Wherein, several compositions are prepared under identical ethanoic acid concentration, grind size of NS seeds and oxygen availability produce similar physical characteristics of their composition. FIG. 19 demonstrate coarsely grinded NS seed extracted with 1.25-1.66% acidity, and FIGS. 20 and 15 demonstrate finely grinded NS seed extracted with ethanoic acid 5% acidity.

D—Pure compounds extracted from NS composition by this novel method that have never been part of the prior art. The pure compounds can be chemically characterized, quantified and studied for safety and efficacy for use in pharmaceutical preparation:

A. Novel white solid precipitate depicted in FIG. 20 (29) that is formed in the jar referred to as example #2 of FIG. 10. Crystallization indicates that the composition reaches a saturation point in relation to one constituent. At this point, a process of precipitation is occurring at the mouth of the container with the formation of a white precipitate sticking to the rubber topper and the glass rim. The taste of this which precipitate is neutral. Precipitation occurs at room temperature. Possible components of NS composition in acid solvent are either alpha-hederin or Nigellidine alkaloid or others.

Figures 23C, 23D:
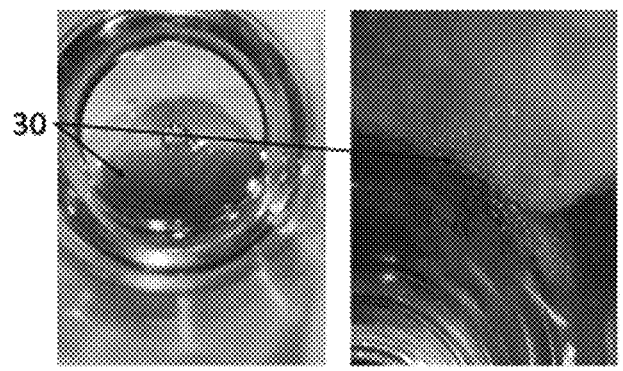

B. Novel water-miscible (mixable) NS oil in the composition (30) which is a lighter clearer oil, wherein, the NS seed oil that forms 30-40% of the seed content is not forming a defined layer floating above the aqueous composition of the bio-fermentation jar. It is rather dispersed in the acid-aqueous phase of the composition. The water-miscible oil (30) can be felt and shines on the cover of the jars depicted in FIG. 23A, when placed on the fingertip as depicted in FIG. 23B, when the composition is evaporated, it leaves the NS water-miscible oil (30) behind as depicted in FIG. 32C and as small dispersed droplets on a glass surface depicted in FIG. 23D. This water miscible oil is thin easily washed away.

Figures 23E, 23F, 23G:
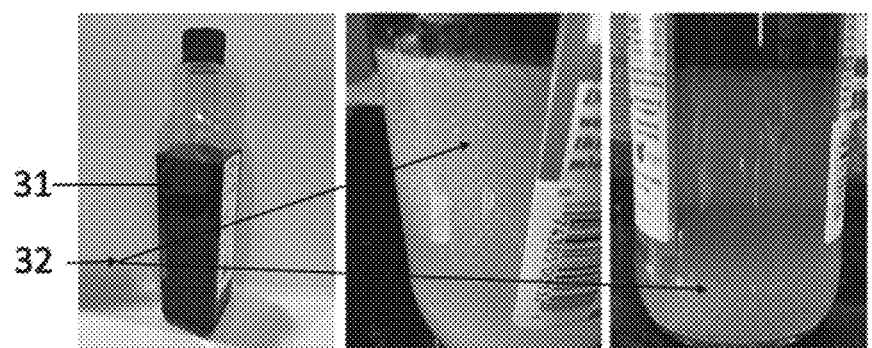
FIG. 23E depicts commercially available NS cold pressed oil with dark black color.
FIG. 23F and FIG. 23G depicts NOVEL crystalized oil droplets moving down in the polar solvent and adhere to the glass surface.

C. Pure novel white crystal-like oil droplets (32) are formed when commercially available NS oil (31) is mixed with ethanoic acid 5% acidity (16) and incubated. The oil droplets are 1-3 millimeters in diameter are moving down into the polar solvent and are not mixable with the solvent. The oil droplets are adherent to the inner glass surface of the container and are scattered as depicted in FIG. 23F. As the droplets grows bigger they settle to the bottom of the container as depicted in FIG. 23G. As a control experiment, olive oil was mixed with vinegar (16), no observable oil droplets were seen. When the NS commercial oil and ethanoic acid solvent are mixed manually for 15-30 minutes a caramel colored emulsion is formed and the crystal-like oil drops appears within the first 30-minutes. Possible components of NS composition that is extracted is the thymoquinone volatile oil or another component.

D. Thick multi-layered new NS mother (24).

Figures 24A, 24B:
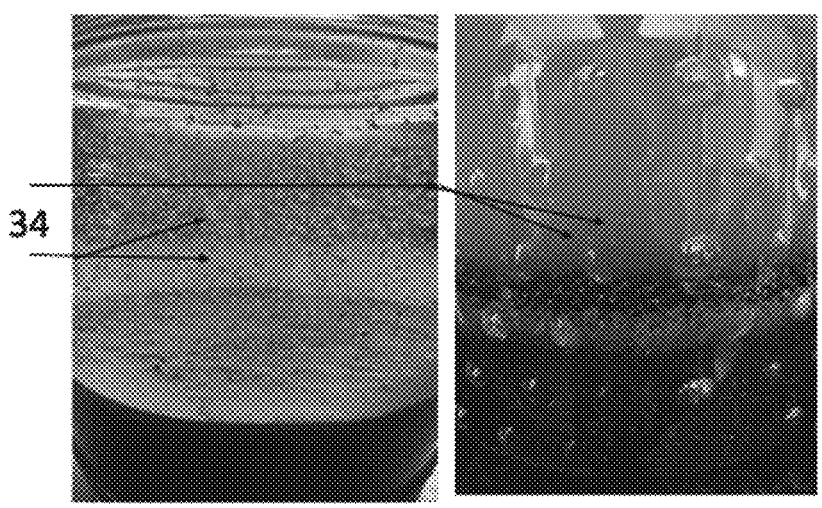
FIG. 24A and FIG. 24B depicts novel floaters in the aqueous solutions (A) and in the emulsion (B).

E. Floaters that are formed in the composition during the incubation period in both the clear composition and the emulsion (34) (FIGS. 24A and 24B)

F. Sticky viscous component that is felt when the composition is concentrated.

G. Bitter component that can be tested when the composition is concentrated.

H. Mucilage (33) seen in FIG. 21.

I. Novel component specifically formed during the acid extraction/bio-fermentation process that can be chemically characterized and are unknown in the prior art.

E—Changes in the volatile oil aroma, wherein the strong acidic stringent aroma of the vinegar and strong NS aroma of the grinded seed become very mild and neutral immediately.

F—Change in the bitter spicy taste of the NS seeds and the acidic vinegar to a milder neutral palatable test.

Mechanisms of the Formation and Stabilization of NS Emulsion Composition

As obvious with other herbal medicines, the extraction methods influence the chemical composition, and consequently, the pharmaceutical activity of a specific NS preparation (Khan and Afzel, 2016).

The NS seed emulsion in ethanoic acid 5% is depicted in FIGS. 10, 14, 15, 20 and 21 and is explained in experiments #2, 4 and 5.

NS emulsion composition consists of two liquids ethanoic acid solvent and NS oil in a mixture that is stable for weeks and months.

I would hypothesize that the extracted composition is both an emulsion and a suspension.

The suspension may refer to fine solid particles floating in the liquid remains dispersed in this thick emulsifies oil-in-liquid extract which make it less clear than pure ethanoic acid solvent.

The emulsion may refer to oil that is suspended in solution.

The solution further comprises oils that are dissolvable in acidic medium of ethanolic acid. The degree of emulsification also affects the color/clarity of the solution. The opacity of the solution increases more insoluble oils are emulsified making the solution have a color that is more milky than marketed ethanolic acid (vinegar) and samples that have suspended solids and dissolved solids. Soluble oils are oils that are extracted from NS and dissolve in the ethanolic acid or the aqueous solution.

The stability of the emulsion can be explained on the following physical/chemical mechanisms: 1—The composition has a high viscosity that is attributed to the presence of the water miscible oil; 2—The Extraction/bio-fermentation of an esterified oil that is water soluble. Esterification is the result of combination of a fatty acid with an alcohol, even ethanoic acid (as a carboxylic acid) can be esterified! It is known that Linn seed oil can be esterified to become water soluble and then used in water paints. 3—Alpha-hederin is a saponin and when it is extracted in the NS composition of this invention can act as stabilizer for NS emulsion extracted by ethanoic acid.

Conversion/Transformation of NS Composition

Some samples appear to have two liquid phases in that have different colors or different opacity. The two-phase liquid system may result from the presence of water in the vinegar which may cause a separation of an aqueous phase in another phase that maybe the vinegar insoluble droplets or oils that are initially dispersed or emulsified in the solution start to agglomerate and form a second and distinguishable liquid phase below the solution. It can be speculated that an oil rich phase comprising vinegar insoluble forms as a separate and independent second liquid phase below the solution that make a thorough or dramatic change in the form, appearance, or character of the product of a transformation.

Gas is liberated from fermentation, both aerobic and anaerobic. which gas? depends on the type of fermentation happening. Gas is liberated from fermentation of sugars and carbohydrates present in NS seeds, both aerobic and anaerobic, it could be $CO_2$ or CO or methane or hydrogen . . . based on the type of fermentation happening, it might be making alcohols too like ethanol or butanol.

It must be noted and appreciated that the instant Invention has been discussed and described in terms of theoretical and experimental aspects to emphasize practical and enabling details. However, our process(s) and product(s) comprise a complex and dynamic bio-organic environment that further includes and comprises: diffusion of liquids (water and acid) into the particles to extract solubles, diffusion of insoluble liquids into the acid/water solvent, agglomeration of insoluble liquid drops to from emulsion into the acid/water phase, dissolution of solubles into acid water, agglomeration of acid/water insoluble to form a second liquid phase that is partially or completely Immiscible with the acid/water phase, aerobic fermentation that may or may not occur concurrently with extraction of oxygen from the solution of vinegar and water to provide oxygen for the aerobic fermentation of carbohydrates, and/or anaerobic fermentation.

In conclusion, broader chemical and biochemical interactions are occurring which allows one of ordinary skill in the art to describe and/or characterize the instant process(s) and product(s) in terms of reaction kinetics, thermodynamic equilibriums, and/or mass transfer rates or limitations. In one aspect, the instant invention comprises reaction kinetic, thermodynamic, and mass transfer characterization of the disclosed process(s) and product(s). Furthermore, chemical identity/structure identification and/or characterizations are also included within the scope of the instant invention.

Analytic Methods used to Identify and Quantify NS Components

Analytic Methods used to Identify and Quantify NS Components of the Composition of the Current Invention are known in the prior art and published studies:

According to Koshak et al., 2018, the thymoquinone concentration of different extracts of NS was analyzed by high-performance liquid chromatography (HPLC). The immunomodulatory activity was assessed by release of mediators in primary human T-lymphocytes, monocytes and A549 human lung epithelial cells.

According to Goyal et al., 2017, the therapeutic potential and pharmaceutical development of thymoquinone molecule.

According to Ajaib M., 2018, a phytochemical screening chemical and biological screening of NS compounds responsible for alkaloids by Mayer's, Wagner's and Hager's tests; terpenoids using Salkowski's method; carbohydrate using Molish's method; steroids using the protocol proposed by Edeoga et al.; antibacterial activities in cultures; and anti-radicle scavenging activities using DPPH and ABTS methods; including quantitative screening of total flavonoids and total phenolic compounds and others.

Other methods known in the art can be used for the detection of different components and the quantitative analysis of NS composition of the current invention.

Advantages of Ethanoic Acid Extraction/Bio-Fermentation of *Nigella sativa* Seed Over Current Solvents In conclusion, this novel process of extracting the bioactive phytochemical constituents from NS seeds using acid extraction/bio-fermentation have demonstrated multiple advantages over existing processes. Theoretically speaking, ethanoic acid with the "mother of vinegar" can produce different effects, not simple extraction, for example, but not limited to:

1. Extraction of unique water-mixable NS oil in the composition.
2. Extraction of unique crystalline salt that fits in the description of alkaloids form NS described by Doughari, 2012. NS alkaloids include Nigellidine.
3. Possible extraction of the water-soluble alpha-hederin in a stable aqueous solution.
4. Extraction of volatile oil thymoquinone in a simple one step, no harsh solvents
5. Pure compounds extracted from NS composition by this novel method that have never been part of the prior art for use in a well-defined pharmaceutical preparation with known content and clear method of quantitation and defined safety and efficacy profile.
6. Ethanoic acid have the to soften plant cellulose (Muthu, 2018) and loosen cell wall for superior extraction.
7. Extracted of unique flocculated protein in acid medium (chemical coagulation). Proteins are considered an important bioactive phytochemical that have not been explored yet!
8. Ethanoic acid is a safe solvent for human consumption; there is no need to use excessive heat to remove it, that could have a deleterious impact on the composition.
9. Ethanoic acid does not leave undesirable smell or taste in the composition.
10. Ethanoic acid does not extract the undesirable black pigment and improve the product's appeal.
11. Vinegar act as a preservative for the composition that keep it stable for long time.

When the Product is Ready for Use as a Complimentary/Pharmaceutical Preparation?

Clear composition can be used within the first day, first week, within 40 days or any time from day 1-day 40 and beyond up to first few years.

Emulsion composition can be used within the first day, first week, within 40 days or any time from day 1-day 40 and beyond up to first few years.

New mother of *Nigella sativa* can be used whenever it is formed.

Pure compounds can be used when they are available within the composition, i.e., the oil droplets appear within the first day and continue to enlarge in size, wherein the white crystalized compound can be seen within weeks, but it is available in smaller amounts before that time.

Instructions for Use of *Nigella sativa* Immunomodulatory/Antiviral Composition to Treat or Prevent COVID-19 Illness:

This invention provides a composition obtained by the process of aqueous ethanoic acid extraction/bio-fermentation and incubation have a high safety profile and is easily accessible to people in need for a medicinal product that boost their own body endogenous mechanisms, empowering the innate immune system from within, to fight COVID-19 illness.

In one embodiment, the composition prepared in accordance with the current method is used to prepare a complimentary medicine, a pharmaceutical drug or a nutritional supplement.

In one embodiment, the composition prepared in accordance with the current method can be formulated in oral dosage forms as a liquid, solution, suspension, emulsion.

In other embodiment, the composition prepared in accordance with the current method can be formulated to a solid dosage forms including, but not limited to, tablets or capsules.

In yet another embodiment, the composition prepared in accordance with the current method is formulated to chewable tablets.

Definitions of the terms used in the instruction for use of this invention Preventive/prophylactic medicine or drug with an intent-to-prevent:

Preventive treatment refers to help avoid disease and maintain health. Using a drug or a composition for disease prevention is a procedure through which individuals, particularly those with risk factors for a disease, are treated in order to prevent a disease from occurring. Treatment normally begins either before signs and symptoms of the disease occur, or shortly thereafter. The preventive effect is mediated via activation of initial IFN-1 secretion and signaling, as "initial alarm" of the innate immune system (Hesary and Akbari, 2020).

Active Pharmaceutical Ingredient (API): Any substance or mixture of substances that becomes pharmacologically active in the drug product formulation to be used in the manufacturing and production of a drug with an intent-to-treat an illness or prevent an illness by enhancing the innate immune response in a human at risk of contracting an infectious disease.

Complimentary drug: *Nigella sativa* medicine can be used along with standard medical treatment but are not considered to be standard treatment. A complimentary medicine such as *Nigella sativa* (black seed) complimentary medicine, do not require "Investigation of New Drug (IND)" filing, and are only promoted on the basis of structure and function but not on the basis of formal medical therapeutic claim to treat specific disease entity (Dajani et al., 2016). The *Nigella sativa* composition extracted by acid extraction/bio-fermentation is intended-for-use as immune booster/enhancer/regulator/inducer/supportive of innate immune responses.

Pharmaceutical excipients: means an ingredient other than the active ingredient. Its standard purpose is to streamline the manufacture of the drug product. Excipients might aid in adjusting the concentration; adjusting the PH (acidity); improve drying; lubricity; flowability; disintegration; taste and may confer some form of antimicrobial function and other manufacturing characteristics known in the prior art.

Enhancement of bioavailability and pharmacodynamic effect of thymoquinone via nanostructured lipid carrier formulation was studied by Elmowafy et al., 2016.

COVID-19 illness: As defined by CDC, is an illness caused by the novel coronavirus with symptoms ranging from asymptomatic patient, mild symptoms to severe illness. Detailed description of clinical presentation of COVID-19 disease is described by McIntosh K., 2020.

TLR-guided intervention strategy: Choudhury and Mukherjee, 2020, studied the involvement of TLRs. especially TLR4 in recognizing molecular pattern of SARS-CoV-2; NS seed extract stimulate the expression of PRRs mainly TLR-4 in rat macrophages (Akrom and Mustofa, 2017); TLR can be triggered by ACE-2 receptor that sense SARS-CoV S protein (Bernstein et al., 2018).

What is interesting is that, several polysaccharides and monoterpenes from the food chain stimulate TLRs, and possibly can be used to treat related diseases (Hug et al., 2018); hence, NS extracts can trigger antiviral immune response to fight COVID-19 illness.

The Composition of this invention: means the complex multi-component *Nigella sativa* extract obtained by the process of acid extraction/bio-fermentation and incubation of this invention that contains ALL the bioactive phytochemicals, as described in the patent application and known in the prior art, or any novel component thereof, for use to manufacture complementary medicines, pharmaceutical drugs or food supplement.

Complimentary medicine of this invention is proposed to induce/booster/enhancer/regulator/support/train/educate the innate immune responses in humans in need for such treatment.

Active pharmaceutical ingredient (API) of this invention is intended-for-use to treat and/or prevent COVID-19 illness acting as an immunomodulator.

Active pharmaceutical ingredient (API) of this invention is intended-for-use to treat and/or prevent COVID-19 illness acting as antiviral.

Active pharmaceutical ingredient (API) of this invention is intended-for-use to treat and/or prevent COVID-19 illness acting as antibacterial (Mahboubi, 2018; Forouzanfaret al., 2014); antitussive and bronchodilator (Ikhsan et al., 2018); Wienkötter N, et al, 2008), antihistaminic antioxidant (Kanter et al., 2006).

Active pharmaceutical ingredient (API) of this invention is intended-for-use to treat and/or prevent COVID-19 illness acting as anti-inflammatory through the action of thymoquinone acting on cytosolic PH and Na+/H+ exchange (NHE) activity in mouse (Yang et al., 2012; Rahmani and Aly, 2015).

Processing of *Nigella sativa* Composition of the Current Invention

The *Nigella sativa* composition obtained by the process of this invention is further processed before its use for the manufacturing of a complimentary or a pharmaceutical drug:

In one embodiment, the liquid composition is centrifuged to remove any particles suspended in the liquid composition.

In one embodiment, the liquid composition is filtered to remove solid particles suspended in the liquid.

In one embodiment, the composition is concentrated by removing water by evaporation under reduced pressure, causing the water to evaporate at a lower temperature than normal or by using other methods known in the art.

In one embodiment, the composition is lyophilized (freeze-dried) to a powder that can be used to prepare the complimentary or pharmaceutical medicine.

In one embodiment, the water miscible oil can be separated by freezing and thawing or other methods known in the art.

In one embodiment, the white solid precipitate component is extracted from the liquid phase by methods known in the art.

In one embodiment, the white crystal-like droplets are collected and used to prepare the complimentary or pharmaceutical medicine.

In one embodiment, the mother of *Nigella sativa* is dried and grinded to a powder or chopped into small pieces or made into a paste for use in the preparation of dosage forms as a single ingredient or in combination with other composition ingredients for example, but not limited to, the oil extracted from the composition.

In one embodiment, the floaters, sticky viscous, bitter or mucilage components are extracted from the liquid phase by methods known in the art can be used to prepare the complimentary or pharmaceutical medicine.

Preparation of Dosage Forms *Nigella sativa* Composition of this Invention

The type and quantity of pharmaceutical additives and procedures used to prepare a complimentary medicine, a pharmaceutical drug or a nutritional supplement will follow the established prior art.

In one embodiment, the product is formulated to a liquid medicine for oral use including, but not limited to, a solution, emulsion or suspension by materials and procedures known in the art.

In one embodiment, the product is formulated to a liquid medicine for oral use including, but not limited to, a solution, emulsion or suspension can be administered via a gastric tube.

In one embodiment, the product is formulated to a solid dosage forms including, but not limited to, tablets or capsules by materials and procedures known in the art.

In one embodiment, the product is formulated to chewable tablets by materials and procedures known in the art.

In one embodiment, the product is formulated to a lyophilized powder that is mixed with water before use by materials and procedures known in the art for pediatric or adult dosage forms.

The Composition of NS of this invention with ANY and ALL the components of NS seeds extracted by ethanolic acid/bio-fermentation and incubation process are prepared in a suitable form for use to treat patients with COVID-19 illness and/or prevent COVID-19 illness. In most embodiments, the NS therapeutic/pharmaceutical preparation is formulated in liquid form for oral dosage known in the art by mixing the liquid composition with pharmaceutically accepted excipients (either inert or active), lipid stabilizer, antacid to adjust the composition PH (acidity), fillers, or any other excipient known in the art making the preparation suitable for therapeutic/pharmacologic use in human.

The excipient may enhance patient experience by offering taste-masking properties. An excipient must best suit the intended dosage form of the preparation.

In one embodiment, the liquid composition is concentrated by evaporation, lyophilization or any method known in the art to get an acceptable dosage volume in cubic centimeters.

In yet another embodiment, the NS therapeutic/pharmaceutical preparation is formulated in to a soft gel capsules for oral dosage by mixing the liquid composition with pharmaceutically accepted excipients (either inert or active), lipid stabilizer, anti-acid to adjust the composition PH (acidity), fillers, or any other excipient known in the art making the preparation suitable for therapeutic/pharmacologic use in human.

In yet another embodiment, the NS therapeutic/pharmaceutical preparation is formulated in to a tablet form for oral dosage by mixing the liquid composition with pharmaceutically accepted excipients (either inert or active), lipid stabilizer, anti-acid to adjust the composition PH (acidity), fillers, or any other excipient known in the art making the preparation suitable for therapeutic/pharmacologic use in human.

In one embodiment, a complimentary/pharmaceutical preparation derived from the composition is also prepared for use as an injection.

In other embodiment, a complimentary/pharmaceutical preparation derived from the composition is also prepared for use as an inhaler to treat human in need for COVID-19 illness.

In other embodiment, a complimentary/pharmaceutical preparation derived from the composition is also prepared for use as local therapy for the eye, skin or to treat human in need for COVID-19 illness.

In yet another embodiment, a complimentary/pharmaceutical preparation derived from the "new NS mother" is also prepared for use as oral dosage form by drying the new NS mother; convert it to a powder; and make capsules or tablets or suspension to be used to treat COVID-19 illness.

In yet another embodiment, a complimentary/pharmaceutical preparation derived from the black pulp of NS extraction process is also prepared for use as oral administration as a food for animals suspected of being hosts or carriers of SARS-CoV-2 virus or in any animal in need for an improved health or other purposes.

*Nigella sativa* Dosage and Administration

The dosage for oral administration of the composition is calculated based on the weight of NS seeds that have been extracted within a defined volume of the composition.

As calculated in table 2, the equation used for calculating the volume of the composition that is equivalent to 1 gram of NS seeds is:

Total volume of the jar X/Weight of NS seeds extracted in jar X=Volume of extract X for use as a single oral dose.

In one embodiment, a single oral dose of *Nigella sativa* used to treat COVID-19 illness is equivalent to 1 gram of the dry seed extracted by the process of this invention.

In one embodiment, the single oral dose of *Nigella sativa* used to treat COVID-19 illness which is equivalent to 1 gram of the dry seed is administered 3-times/day (8-hour dosing).

In one embodiment, the single oral dose of *Nigella sativa* used to treat COVID-19 illness which is equivalent to 1 gram of the dry seed three timed/day is administered for a duration of 7-14 days.

Expected Onset of Therapeutic Action

The importance of the onset of INF responses relative to virus replication is vital is key factor in determines coronavirus outcomes:

The current inventor in previous patent, treating virus-induced asthma exacerbations and allergic rhinitis with *Nigella sativa* or AM3, have found that the onset of clinical improvement in cough, sputum and shortness of breath of *Nigella sativa* or AM3 started in day 3 ((UK patent publication #GB2348139, granted in 2004, PCT, and U.S. Pat. No. 7,592,327, B2).

According to Salem and Hossain. 2000; Forouzanfar et al., 2014, treatment of murine cytomegalovirus (CMV) infection with intraperitoneal NS oil for 7 days strikingly inhibited the virus titers in spleen and liver on day 3 of infection. This coincided with an increase in serum level of IFN-gamma. On day 10 of infection, the virus titer was undetectable in spleen and liver. increased numbers of CD4+ helper T cells.

The importance of the onset of INF responses relative to virus replication is vital is key factor in determines coronavirus outcomes; INF-1 administration within 1 day after infection (before virus titer peak) protected mice from lethal SARS-CoV infection. If present early and properly localized, IFN-1 can effectively limit CoV infection (Channappanavar et al., 2019). Differences in the dynamics of interferon-related innate immune responses in children, adults and elderly may explain the reported difference in fatality rates; earlier induction of interferons in children could be the reason behind zero fatality (Nezhad et al., 2020). An early burst of type I IFN leads to protection. In contrast, a delay in IFN production causes an inability to control viral replication, leading to cellular damage and cytokine storm. The delay in response often predominates in older adults making them more susceptible to emerging infections Nikolich-Zugich et al., 2020. Interferons orchestrate local and systemic antiviral state (Denney and Ho, 2018).

Assessment of Beneficial Outcomes

Clinical Primary Endpoints:

There are general endpoints that are used in ongoing clinical trials, e.g., Honey & *Nigella sativa* Trial Against COVID-19 (HNS-COVID-PK); Clinicatrials.gov Identifier: NCT04347382. Investigators will follow up with participants every 4th day to access clinically the severity of symptoms along with RT-PCR and HRCT chest or X-ray to access the disease progression. Those positive on 8th day will be followed up further for monitoring of primary end points. Findings of this trial are expected to help establishing a new remedy for the treatment of this pandemic giving mortality benefit along with earlier decrease in viral load and lesser complications rate caused by SARS-Cov-2 virus. Other clinical and laboratory endpoints known in the art can be used.

Specific laboratory endpoints in vivo and in vitro:

A—Interferon serum level measurement performed using patient's blood samples

B—Complete blood count to demonstrate reversal of the lymphopenia

C—Flow cytometry can be conducted to detect the number of specific cell type of the innate immune cells in patient's blood samples D—Viral RNA level using polymerase chain reaction (PCR).

E—Activation status of natural killer cells as an early responder to virus infection and their level is significantly reduced in the lung of COVID-19 patients (Duijf P., 2020).

F—The composition can be studied for activation status of natural killer cells (described by Grudzien and Rapak, 2018) or maturation of dendritic cells and the inhibition of viral replication in cell line known in the art.

*Nigella sativa* Safety for Human Use

The safety of *Nigella sativa* is based on the Code of Federal Regulation (CFR21) and published studies (Aftab et al, 2013; Barakat et al, 2013 and Yimer et al., 2019).

Indication for Use of *Nigella sativa* Composition of this Invention

Due to the safety and easy accessibility of a complimentary drug and pharmaceutical preparation manufactured using *Nigella sativa* composition of this invention make it a potentially successful therapeutic invention:

1. An innate immunity booster supplement for oral rout of administration
2. Treatment of "probable" patients at the very early stage of the disease, contrary to all currently available treatment that are indicated for hospitalized patients.
3. Available for patients as an outpatient treatment and for telemedicine.
4. Treat confirmed COVID-19 patients (as defined by CDC 2020 Interim Case Definition approved Apr. 5, 2020) as an add-on therapy with the standard protocol.
5. Used as a preventive treatment for the following indications:
   a. Older adults,
   b. Chronically ill patients with higher risk of serious illness with COVID-19,
   c. Healthcare professionals caring for COVID-19 µl patients and caregivers,
   d. Close contacts and family members of COVID-19 illness,
6. Asymptomatic carriers transmitting SARS-CoV-2 virus, hence limiting the spread of the virus to healthy individuals.
7. Treatment of loss of smell and taste as part of the COVID-19 illness.

8. On the counter complimentary drug.

9. Treating animal reservoir of COVID-19 virus.

Combination Composition: A composition comprising two constituents derived from *Nigella sativa* seeds for example, but not limited to, a product consisting of the active ingredient alpha-hederin and nigellidine in a concentration capable of treating and preventing COVID-19 illness in a human or animal in need for such treatment.

A combination composition consisting of the unique extracted products of the extract in concentrations and proportions capable of treating and preventing COVID-19 illness with or without the water miscible oil.

A Combination composition consisting of *Nigella sativa* miscible oil and synthetic alpha-hederin.

A combination composition consisting of *Nigella sativa* miscible oil and synthetic nigellidine.

The combination is speculated to prove effective either in an additive manner, or a synergistic manner, or as a booster to the immunomodulatory therapeutic effects of this invention in the treatment or prevention of COVID-19 illness.

As part of the patent filed by the current inventor in 1999 (U.S. Pat. No. 7,592,327) AM3 was selected because it is an immunomodulator that induce interferon production, activate NK, and induce DCs maturation. AM3 is described in the Martindale Extended Pharmacopeia). AM3 is known as glycophosphopeptical marketed by Industrial Farmaceutica Cantabria. Also known as glicofosfopeptical, polysubstituted polycarboxylic phosphamide biopolymers or GPP and produced by Industria Farmaceutica Andromaco. The difference in the method of use of AM3 in the prior vs. the current use is that AM3 was used continuously for periods of months vs. in the current invention AM3 combination with extracts of the current invention is preferably used for a short duration of days or 2-3 weeks. In one embodiment, the instant *Nigella sativa* product can be used in combination with glycophosphopeptical (AM3). The disclosure of US patent (U.S. Pat. No. 7,592,327, B2) is considered relevant and is incorporated herein in its entirety. The combination is speculated to prove effective either in an additive manner, or a synergistic manner, or as a booster to the immunomodulatory therapeutic effects of this invention in the treatment or prevention of COVID-19 illness.

What is claimed is:

1. A product obtained by a process of acid extraction, emulsification, and biofermentation of bioactive phytochemical compounds from *Nigella sativa*, comprising:

grinding parts of a *Nigella sativa* plant;

soaking the parts in an aqueous acid solvent for at least one hour to obtain a water-miscible oil, wherein the acid solvent comprises aqueous ethanoic acid with or without mother of vinegar, wherein alpha-hederin from the parts is dissolved in an aqueous phase of the solvent to form a composition;

adjusting the acidity of the acid solvent to a range of 0.1-20%, volume by volume, and incubating the composition in anaerobic or aerobic conditions for at least one day, wherein incubating comprises a fermentation process to form alcohol.

2. The product of claim 1, wherein:

the parts comprise finely-ground seeds;

the acidity of the acid solvent is 5-20% in water; and after incubation, the composition is an emulsion having an opaque, milky appearance, the composition comprising the water-miscible oil, components soluble in an oil phase, components soluble in the aqueous phase, and saponin.

3. The product of claim 2, wherein the emulsion is formulated into a pharmaceutical product intended for use to treat COVID-19.

4. The product of claim 1, wherein:

the parts comprise coarsely seeds;

the acidity of the acid solvent is about 0.1-2.5%; and after incubation, the composition has a transparent, honey-colored appearance and comprises the water-miscible oil, components soluble in an oil phase, components soluble in the aqueous phase, and saponin.

5. The product of claim 4, wherein the composition is formulated into a pharmaceutical product intended for use to treat COVID-19.

6. The product of claim 1, wherein:

the parts comprise seed oil;

the acidity of the acid solvent is about 5-20%; and after incubation, the composition comprises crystal-like droplets in the acid solvent.

7. The product of claim 1, wherein:

the parts comprise seeds, wherein the seeds are coarsely ground;

the acidity of the acid solvent is about 5-20%; and after incubation, the composition comprises a white solid precipitate.

8. The product of claim 1, wherein:

the parts comprise seeds;

the acidity of the acid solvent is about 0.1-20%; and after incubation, the composition comprises mother of *Nigella sativa.*

9. The product of claim 1:

wherein alcohol formed in during fermentation in the presence of ethanoic acid forms an ester of extracted fatty acids.

10. The product of claim 9, wherein the fatty acid esters are water-miscible.

11. The product of claim 9, further comprising ester linked thymoquinone.

12. A product obtained by a process of acid extraction, biofermentation, and emulsification of bioactive phytochemical compounds from *Nigella sativa*, comprising:

grinding parts of a *Nigella sativa* plant;

soaking the parts in an acid solvent, wherein the acid solvent comprises aqueous ethanoic acid to form an emulsion, wherein the acid solvent has an acidity of 0.1-20%, volume by volume;

incubating the mixture in anaerobic or aerobic conditions to form water-miscible fatty acids extracted from the parts of the *Nigella sativa* plant.

* * * * *